US006410756B1

(12) United States Patent
Zamir et al.

(10) Patent No.: US 6,410,756 B1
(45) Date of Patent: *Jun. 25, 2002

(54) FAMILY OF CANADENSOL TAXANES, THE SEMI-SYNTHETIC PREPARATION AND THERAPEUTIC USE THEREOF

(75) Inventors: Lolita Zamir, Westmount; Gaéton Caron, Laval, both of (CA); Yi Feng Zheng, Salt Lake City, UT (US)

(73) Assignee: Institut National de la Recherche Scientifique, Sainte-Foy (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/957,138

(22) Filed: Oct. 24, 1997

(30) Foreign Application Priority Data

Oct. 24, 1996 (CA) .............................................. 2188714
Feb. 12, 1997 (CA) .............................................. 2197369

(51) Int. Cl.[7] .......................................... C07D 305/14
(52) U.S. Cl. ........................ 549/510; 549/511; 549/214
(58) Field of Search ................................ 549/510, 511, 549/214

(56) References Cited

U.S. PATENT DOCUMENTS

| 4,924,011 A | | 5/1990 | Denis et al. ................. 549/510 |
| RE34,277 E | | 6/1993 | Denis et al. ................. 549/510 |
| 5,319,112 A | | 6/1994 | Kingston et al. ............. 546/510 |
| 5,399,726 A | * | 3/1995 | Holton et al. ................ 549/510 |
| 5,440,047 A | | 8/1995 | Nishimura et al. .......... 546/344 |

FOREIGN PATENT DOCUMENTS

| CA | 2095375 | 11/1993 |
| EP | 0 534 709 A1 | 3/1993 |
| EP | 0 625 517 A1 | 11/1994 |
| FR | 2 697 522 A1 | 5/1994 |
| WO | WO 92/09589 A1 | 6/1992 |
| WO | WO 93/21173 A1 | 10/1993 |
| WO | WO 94/13654 A1 | 6/1994 |
| WO | WO 94/13655 A1 | 6/1994 |
| WO | WO 94/21251 A1 | 9/1994 |
| WO | WO 94/21651 A1 | 9/1994 |
| WO | WO 95/02400 A1 | 1/1995 |
| WO | WO 95/33736 A1 | 12/1995 |

OTHER PUBLICATIONS

Georg et al, "Biorganic Medicinal Chemistry Letters", vol. 4, No. 2, pp. 335–338, 1994.*

Denis, J.–N. And A.E. Greene, "A Highly Efficient, Practical Approach to Natural Taxol," *J. Am. Chem. Soc.* 110:5917–5919 (1988).

Denis, J.–N. et al., "An Improved Synthesis of the Taxol Side Chain and of RP 56976," *J. Org. Chem.* 55:1957–1959 (1990).

Georg, G.L. et al., "Schotten–Baumann acylation of N–debenzoyltaxol; an efficient route to N–acyltaxol analogs and their biological evaluation," *Chem. Abstracts* 120:30–31, Abstract No. 315283v (1994).

Kerns, E.H. et al., "Profiling new taxanes using LC/MS and LC/MS/MS substructural analysis techniques," *Chem. Abstracts 124*:Abstracts 124:Abstract No. 343718a (1996).

Ojima, I. et al., "New and Efficient Approaches to the Semisynthesis of Taxol and Its C–13 Side Chain Analogs by Means of β–Lactam Synthon Method," *Tetrahedron* 48:6985–7012 (1992).

Ojima, I. et al., "A Highly Efficient Route to Taxotere by the β–Lactam Synthon Method," *Tetrahedron Letters* 34:4149–4152 (1993).

English language abstract of French Patent No. 2,697,522, May 6, 1994.

* cited by examiner

*Primary Examiner*—Ba K. Trinh
(74) *Attorney, Agent, or Firm*—Sterne, Kessler, Goldstein & Fox P.L.L.C.

(57) ABSTRACT

The present invention relates to a new taxane having the structure as in Formula I, and its analogs as depicted in Formula II and Formula III. The invention includes novel semi-synthetic and isolation methods for the preparation of these novel taxanes. Specifically, the present invention relates to the new taxane Canadensol isolated from plants of the Taxus genus in particular, *Taxus canadensis*. The present invention further relates to the use of these new taxanes as anticancer agents.

21 Claims, 9 Drawing Sheets

Microtubule assay

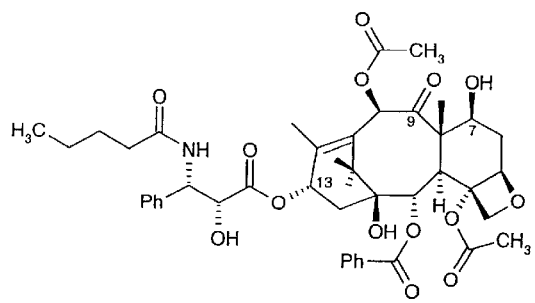

| Position | δ (H)-mult | J(Hz) | δ (C)-HMQC | HMBC | NOESY |
|---|---|---|---|---|---|
| 1 | — | | 78.8 | | |
| 2 | 5.681 (d) | 7.1 | 74.9 | C1, C3, C8, C14, C15, 166.9 (Bz) | H3, H20b, H6b, Me19, Me17, H7' |
| 3 | 3.787 (d) | 7.1 | 45.2 | C1, C2, C5, C8, C19, C20 | H2, H7, H10, Me14a, Me18 |
| 4 | | | 81.1 | | |
| 5 | 4.940 (br.d) | 8.6 | 84.2 | | |
| 6a 6b | 2.544 (ddd) 1.86 (om) | 15.2, 9.8, 7.1 | 35.2 | | H5, H7, H6b |
| 7 OH-7 | 4.403 (m) 2.460(d) | 3.9 | 71.9 | Me19, C6 | H10, H3, H6a, H5, OH7 H7, H10,Neg: OH2', OH1 |
| 8 | | | 58.5 | | |
| 9 | | | 203.6 | | |
| 10 | 6.280(s) | | 75.4 | C9, C11, C12, C15, 171.2 | H7, Me18, H3 |
| 11 | | | 133.0 | | |
| 12 | | | 141.8 | | |
| 13 | 6.206(o.t) | | 72.2 | | H14b,(2.28),Me16 |
| 14 | 2.30(o.m.) | | 35.2 | | 2.34a: H2', H3',H3 , Me18 2.30b,H10, H3 |
| 15 | | | 43.1 | | |
| 16 | 1.269(s) | | 26.4 | C1, C11, C15, C17 | H13, H14b, Me19 |
| 17 | 1.155(s) | | 21.7 | C1, C11, C15, C16 | H2, Me18, Me19, Me16 |
| 18 | 1.823(s) | | 14.7 | C11, C12, C13 | H10, H3,H7, 14a |
| 19 | 1.681(s) | | 9.4 | C3, C7, C8, C9 | H2, H20b, H6b, Me17 |
| 20a 20b | 4.299(d) | 8.3 8.3 | 76.3 | C4 C5 | H7, H20b, Bz-o H2, Me19, H20a |
| 1' (CO) | — | | | | |
| 2' (CH-OH) OH-2' | 4.680(dd) 3.443(d) | 5.1, 2.7 5.1 | 72.8 | | H3', OH2', H14a (2.33), Ph NH4', H2', OH7/OH1 (Neg) |
| 3' (CH-Ph) Ph | 5.575(dd) 7.42 7.32(m) | 8.5, 2. | 54.3 128.9, 126.8 128.3 | 137.9, | NH, H2', H14a (2.33), Ph |
| 4' (NH) | 6.196(o.d) | ≈9 | | | H3', H14b,H6', Me16 (see H10) |
| 5' (CO) | — | | | | |
| 6' (CH2) | 2.205 (t) | 7.5 | 36.1 | | NH4' |
| 7' (CH2) | 1.54(o.m.) | | 27.6 | | H6' |
| 8' (CH2) | 1.296(o.qu.) | 7.5 | 22.0 | | |
| 9' (CH3) | | 7.5 | 13.5 | C7', C8' | |
| O-Bz (2) o- m p | — 8.116(d) 7.509(t) 7.617(t) | 7.3 7.8 7.1 | 166.9 130.0 128.6 133.6 | 166.9 | |
| Ac | 2.345 (s) 2.248 (s) | | 22.3 20.5 | 170.2 171.2 | |
| OH-1 (s) | 1.878 | | | | |

FIG. 5

* p<0.01
Drug was injected iv on day 1 and day 3

FAMILY OF CANADENSOL TAXANES, THE SEMI-SYNTHETIC PREPARATION AND THERAPEUTIC USE THEREOF

FIELD OF THE INVENTION

The invention relates to novel taxanes, semi-synthetic and isolation methods for their production and their use an anticancer agents.

BACKGROUND OF THE INVENTION

The taxane family of terpenes are considered as an exceptionally promising group of cancer chemotherapeutic agents. Many taxane derivatives are highly cytotoxic and possess strong in vivo activities in a number of leukemic and tumor systems.

The best known taxane is paclitaxel (Bristol-Myers Squibb's Taxol®). Currently, paclitaxel and semisynthetic analog docetaxel (Rhône Poulenc Rorer's Taxotere®) have been approved for the treatment of breast and ovarian cancer, and many clinical trials are underway for a number of other indications, including lung cancer, Kaposi's sarcoma, and lymphoma.

A major problem with all of the clinical studies is the limited availability of the compounds. Paclitaxel is a natural product which can be isolated from the bark of Yew trees, but the extraction is difficult, the process is expensive and the yield of paclitaxel is low. Removal of the bark destroys Pacific or Western yew, *Taxus brevifolia*, which is listed among the world's endangered conifer species. The original method of obtaining Taxol® involved cutting down and stripping tens of thousands of trees to harvest small amounts of the compound (13,500 kg of *Taxus brevifolia* bark yields about 1 kg of paclitaxel). Alternative modes of obtaining paclitaxel have not solved the supply problem. The total chemical synthesis of paclitaxel requires more than thirty steps. Taxus plant cell culture only supplies relatively low yields of taxanes, and biosynthesis by a yew tree fungus, *Taxomyces andreanae* has not been sufficient to be economically feasible (Nature Biotech., 14:1055, 1996).

Isolation of taxanes from the stems and needles of various Taxus species offers hope that the supply of taxanes, which can be used for semi-synthesis, will become more abundant. Because of the structural complexity of paclitaxel, partial synthesis is a far more viable approach to providing adequate supplies of paclitaxel and paclitaxel precursors and derivatives than total synthesis. The first successful partial synthesis of paclitaxel was developed by Denis et al, (U.S. Pat. No. 4,924,011 re-issued as 34,277) using the starting material 10-deacetylbaccatin III which can be extracted in relatively high yield from needles of specific species of *taxus baccata*.

Many derivatives of paclitaxel have also been synthesized since the realization of its utility as a therapeutic agent in the treatment of cancer. Examples include 7-deoxy-taxol analogs (as described in PCT Application No. WO 94/13655), which are useful for breast, ovarian, lung, colonic and gastric cancers, malignant melanoma and leukemia. A number of benzoate derivatives (Canadian Patent Application No. 2,095,375), have also been synthesized. Paclitaxel analogs with a ketone moiety (U.S. Pat. No. 5,440,047 and PCT Application No. WO 95/33736), have also been reported to have remarkable antitumoral and antileukemic properties. Derivatives with an epoxide residue have also been disclosed (PCT Application No. WO/94/13654) which exhibit antitumour activity. The preparation of a further group of taxane derivatives have been described in PCT Application Nos. WO 95/02400 and WO 93/21173 which are structurally very similar to paclitaxel but have somewhat increased chemotherapeutic activity when compared to paclitaxel.

Although the use of paclitaxel is successful against a number of specific tumor types, it is not universally effective. Different taxanes exhibit different efficacies to various tumor types, hence there is an urgent need for novel compounds from the taxane family that are closely related to paclitaxel in their chemical structures but which have more potent chemotherapeutic activities.

SUMMARY OF THE INVENTION

One embodiment of the present invention is to provide a new taxane and its derivatives, which have chemotherapeutic activities.

A further embodiment of the present invention is to provide a compound, hereinafter referred to as Canadensol, having the following structural Formula I:

Formula I

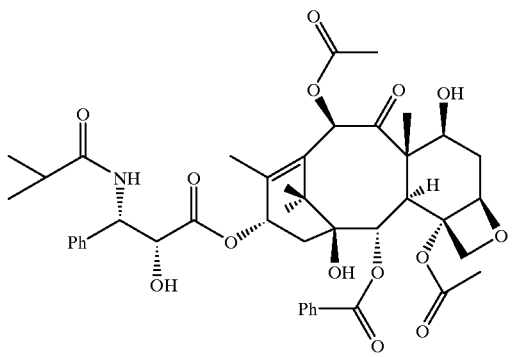

a previously unknown constituent of the Canada yew, *Taxus canadensis*.

It is another embodiment of the invention to provide analogs having in common with Canadensol the following structural Formula II:

Formula II

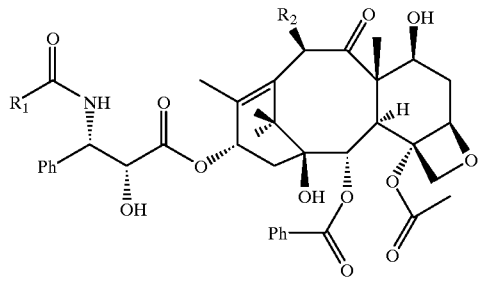

as well as a process for preparing such compounds from the starting material baccatin III.

Wherein: $R_1$ in Formula II is selected from the group consisting of: $C_1$–$C_6$ alkyl including methyl, isopropyl, isopropenyl, propenyl, butyl, cyclopropyl, substituted alkyl including halo, di-(tri-halomethyl)methyl, 3'-trihalo-n-propyl, or phenyl substituted with: one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, 2-furyl, 2-thienyl; 1-napthyl, 2-napthyl, isopropoxy, isopropenoxy, propenoxy, cyclopropoxy, di-(trihalomethyl)methoxy, 3'-trihalo-n- propanoxy, dimethylamino, ethylamino, isopropylamino, propylamino, isopropenamino, imidazol, acetyl, hydroxycarbonyl, 2-(hydroxy)ethyl, 2-(methyl)-propyl, benzyl.

Wherein: $R_2$ in Formula II is selected from the group consisting of: —OAc or —OH.

It is a further embodiment of the present invention to provide analogs having in common with Canadensol the following structural Formula III:

Formula III

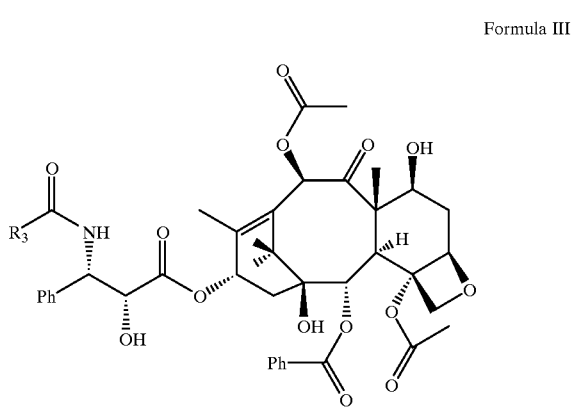

as well as a process for preparing such compounds from the starting material baccatin III.

Wherein: $R_3$ in Formula III is selected from the group consisting of: $C_1$–$C_6$ alkyl including methyl, isopropenoyl, isopropenoyl, propenoyl, cyclopropanoyl, substituted alkyl including halo, di-(tri-halomethyl)acetanoyl, 3'-trihalo-n-propanoyl, 3,4-methylene-dioxyphenyl or phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, 2-furyl, 2-thienyl, 1-napthyl, 2-napthyl, isopropoxycarbonyl, isopropenoxycarbonyl, propenoxycarbonyl, cyclopropoxycarbonyl, di-(trihalomethyl)methoxycarbonyl, 3'-trihalo-n-propanoxycarbonyl, dimethylaminocarbonyl, ethylaminocarbonyl, isopropylaminocarbonyl, propylaminocarbonyl, isopropenaminocarbonyl, imidazolcarbonyl, pyruvyl, oxalyl, 2-(hydroxy) ethylcarbonyl, 2-(methyl)-propylcarbonyl, benzylcarbonyl.

Due to the immediate requirement for additional novel taxanes, a further object of the present invention is to provide a family of taxanes, represented by Formula II and Formula III. These compounds are useful for the treatment of, or in the preparation of paclitaxel derivatives for use in treatment of, cancers and leukemias. The invention also provides for pharmaceutically acceptable compositions compounds of Formula II and Formula III, for use as therapeutic agents for use as anticancer agents in the management of such disease.

It is a further embodiment of this invention to provide a simple and inexpensive semi-synthetic method for the production of these novel taxanes. Accordingly, it is an object of this invention to provide a reproducible method for the isolation and semi-synthesis of taxanes from plant matter derived from the Taxus genus of plants.

Yet a further object of the present invention is to provide, in particular a method for the isolation and semi-synthesis of a novel taxane, named Canadensol, which exhibits higher chemotherapeutic activity than paclitaxel.

It is a further object of this invention to provide a method for the production of a number of protected intermediates, that are useful in the semi-synthesis of novel taxanes.

It is yet a further embodiment of the present invention to provide for the use of the compounds exhibited in Formula I, II, and III in the treatment of various maladies, including various forms of cancer.

These and other objectives, as well as the nature, scope and utilization of this invention, will become readily apparent to those skilled in the art from following the description, the drawings and the appended claims.

BRIEF DESCRIPTION OF THE DRAWINGS

The present invention is disclosed in connection with the appended drawings, in which:

FIG. 5 shows the NMR data of N-debenzoyl-N-n-pentanoyl-paclitaxel;

FIG. 10 shows an NMR spectrum of:

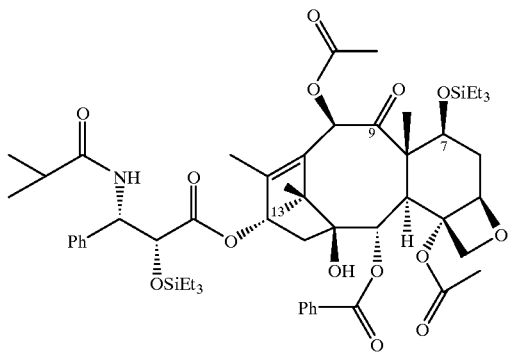

DETAILED DESCRIPTION OF THE INVENTION

Figure 1:
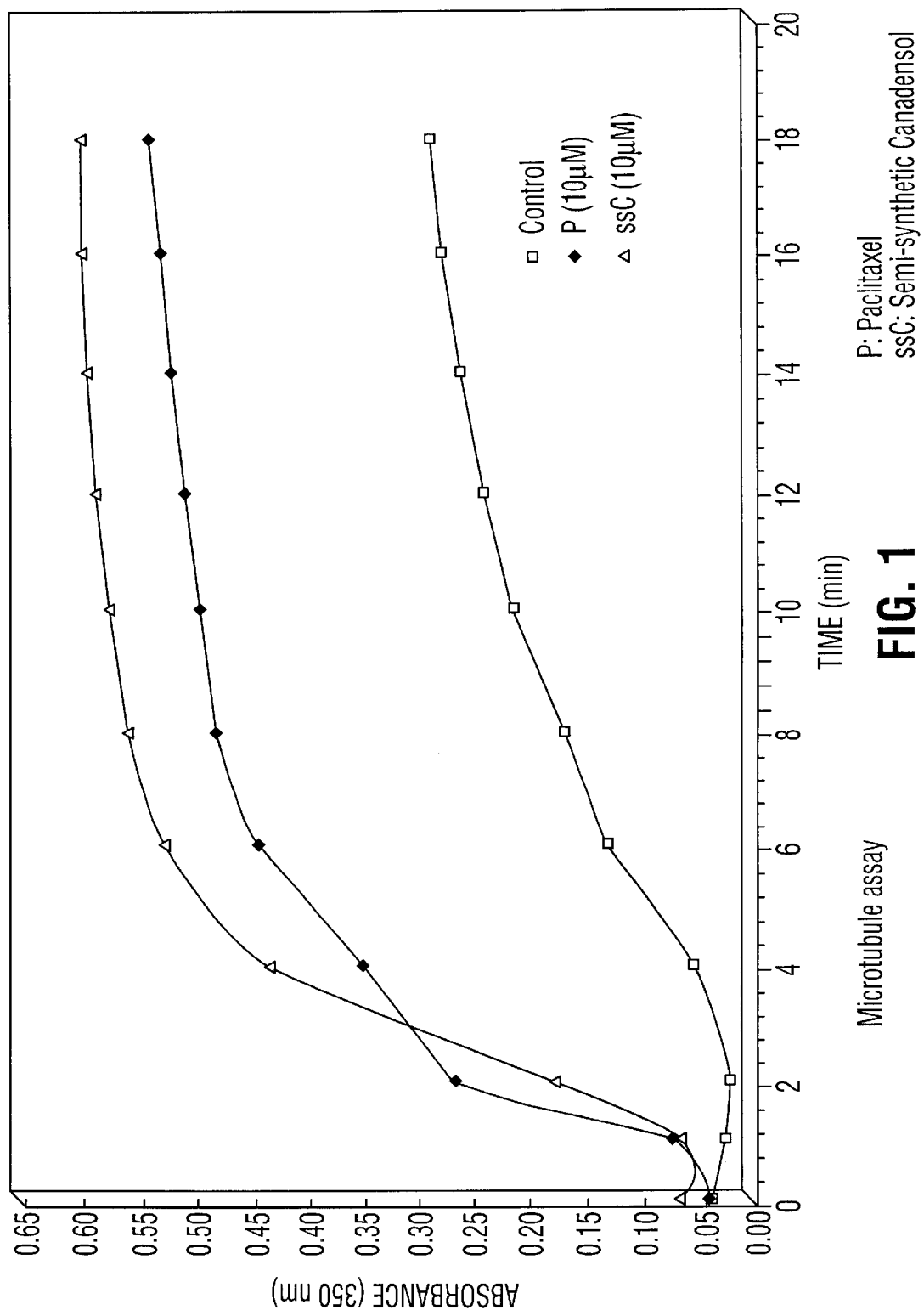
FIG. 1 shows the results of a microtubule assay indicating that Canadensol exhibits a higher antimitotic activity than paclitaxel at the same concentration.

The present invention comprises the compound Canadensol as well as derivatives thereof, having the structure Formula II and Formula III:

Formula II

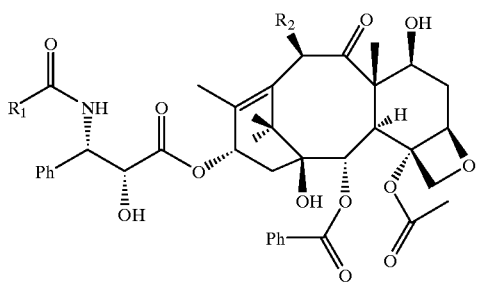

Wherein: R₁ in Formula II is selected from the group consisting of: $C_1$–$C_6$ alkyl including methyl, isopropyl, isopropenyl, propenyl, propyl, butyl, cyclopropyl, substituted alkyl including halo, di-(tri-halomethyl)methyl, 3'-trihalo-n-propyl, or phenyl substituted with: one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, 2-furyl, 2-thienyl; 1-napthyl, 2-napthyl, isopropoxy, isopropenoxy, propenoxy, cyclopropoxy, di-(trihalomethyl) methoxy, 3'-trihalo-n-propanoxy, dimethylamino, ethylamino, isopropylamino, propylamino, isopropenamino, imidazol, acetyl, hydroxycarbonyl, 2-(hydroxy)ethyl, 2-(methyl)-propyl, benzyl.

Wherein: R₂ in Formula II is selected from the group consisting of: —OAc or —OH.

It is also another object of the invention to provide analogs having in common with Canadensol the following structural Formula III:

Formula III

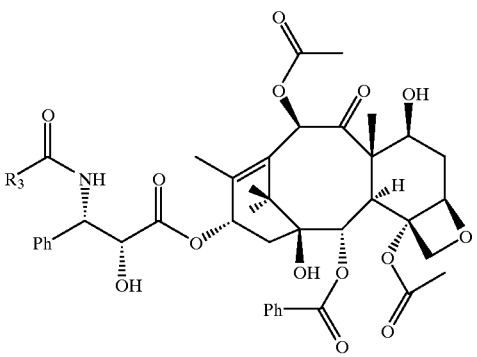

as well as a process for preparing such compounds from the starting material baccatin III.

Wherein: R₃ in Formula III is selected from the group consisting of: $C_1$–$C_6$ alkyl including methyl, propyl, isopropyl, butyl, 1'-methyl-propyl, 2'-methyl-propyl, pentyl and all possible stereoisomers; isopropanoyl; isopropenoyl, propenoyl, cyclopropanoyl, substituted alkyl including halo, di-(tri-halomethyl)acetanoyl, 3'-trihalo-n-propanoyl, 3,4-methylene-dioxyphenyl or phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, 2-furyl, 2-thienyl, 1-napthyl, 2-napthyl, isopropoxycarbonyl, isopropenoxycarbonyl, propenoxycarbonyl, cyclopropoxycarbonyl, di-(trihalomethyl)methoxycarbonyl, 3'-trihalo-n-propanoxycarbonyl, dimethylaminocarbonyl, ethylaminocarbonyl, isopropylaminocarbonyl, propylaminocarbonyl, isopropenaminocarbonyl, imidazolcarbonyl, pyruvyl, oxalyl, 2-(hydroxy) ethylcarbonyl, 2-(methyl)-propylcarbonyl, benzylcarbonyl.

The following definitions apply to these compounds and throughout the present disclosure.

The term "alkyl" as used herein refers to a monovalent group derived by the removal of a single hydrogen atom from a straight- or branched-chain saturated hydrocarbon containing one to six atoms including, but not limited to, methyl, ethyl, n- and iso-propyl, n-, sec-, iso- and tert-butyl, pentyl and hexyl.

The term "substituted alkyl" as used herein refers to an alkyl group as defined above substituted with between one and three groups such as hydroxyl, sulfhydryl, alkoxyl, carboxyl and halogen.

The term "alkoxy" as used herein refers to an alkyl function as defined above attached via an oxygen atom including, but not limited to, methoxy, ethoxy, iso-propoxy, butoxy and tert-butoxy.

The term "substituted alkoxy" as used herein refers to an alkoxy group as defined above substituted with between one and three groups such as hydroxyl, sulfhydryl, alkoxy, thioalkoxyl, carboxyl, amino and halogen.

The term "alkoxyalkyl" as used herein refers to an alkoxy function as defined above attached to an alkyl group including, but not limited to, methylpropionoyl and ethylbutanoyl.

The term "alkanoyl" as used herein refers to an alkyl function as defined above attached via a carbonyl group including, but not limited to, acetoyl, propionyl, butanoyl and isobutanoyl.

The term "hydroxyalkyl" as used herein refers to an alkyl function as defined above substituted with between one to three hydroxyl groups including, but not limited to, hydroxyethyl and hydroxypropyl.

The term "cycloalkyl" as used herein refers to an alkyl function as defined above where some of the carbon atoms are joined to form a ring including, but not limited to, cyclopropyl, cyclobutyl and cyclopentyl.

The term "alkenyl" as used herein refers to an alkyl function as defined above which contains between one and three unsaturated bonds including, but not limited to, isopropenyl.

The term "phenoxy" as used herein refers to an phenyl group as defined above attached via an oxygen atom.

The term "aminoalkyl" as used herein refers to an alkyl function as defined above substituted with amino or substituted amino, as defined elsewhere herein.

The term "aminoalkanoyl" as used herein refers to an alkanoyl function as defined above substituted with between one and three amino groups including, but not limited to, 2-aminopropanoyl, 4-aminobutanoyl, and 6-aminohexanoyl. Additionally, the amino groups may optionally be substituted with peptidyl residues formed therefrom.

The term "substituted alkoxyalkyl" as used herein refers to an alkoxyalkyl group as defined above substituted with between one and three groups such as hydroxyl, sulfhydryl, alkoxyl, thioalkoxyl, carboxyl, amino and halogen.

The term "substituted alkanoyl" as used herein refers to an alkanoyl group as defined above substituted with between one and three groups such as hydroxyl, sulfhydryl, alkoxyl, carboxyl and halogen.

The term "substituted hydroxyalkyl" as used herein refers to an hydroxyalkyl group as defined above substituted with between one and three groups such as sulphydryl, carbonyl and halogen.

The term "substituted cycloalkyl" as used herein refers to an cycloalkyl group as defined above substituted with between one and three groups such as hydroxyl, sulfhydryl, alkoxyl, thioalkoxyl, carboxyl, amino and halogen.

The term "substituted alkenyl" as used herein refers to an alkenyl group as defined above substituted with between one and three groups such as hydroxyl, sulfhydryl, alkoxy, thioalkoxyl, carboxyl, amino and halogen.

The term "substituted phenyl" as used herein refers to a phenyl group substituted with between one and three substituents independently selected from alkyl, halogen, haloalkyl, alkoxy, benzyloxy, thioalkoxy, hydroxy, alkanoyl, carboxy, amino, alkylamino, dialkylamino, nitro and $-OSO_3H$.

The term "substituted phenoxy" as used herein refers to a phenoxy group substituted with between one and three substituents independently selected from alkyl, halogen, haloalkyl, alkoxy, benzyloxy, thioalkoxy, hydroxy, alkanoyl, carboxy, amino, alkylamino, dialkylamino, nitro and $-OSO_3H$.

The term "substituted amino" as used herein refers to an amino group substituted with one or two alkyl groups including, but not limited to, t-butylamino, benzylamino and N,N-dimethylamino.

The term "substituted aminoalkyl" as used herein refers to an aminoalkyl group substituted with between one and three groups including, but not limited to, hydroxyl, sulfhydryl, alkoxyl, thioalkoxyl, carboxyl, amino and halogen.

The term "substituted aminoalkanoyl" as used herein refers to an aminoalkanoyl group substituted with between one and three groups including, but not limited to, hydroxyl, sulfhydryl, alkoxyl, thioalkoxy, carboxyl, amino and halogen.

The term "substituted imidazol" as used herein refers to an imidazol group substituted with between one and three groups including, but not limited to, hydroxyl, sulfhydryl, alkoxyl, thioalkoxyl, carboxyl, amino and halogen.

The term "halogen" as used herein refers to a group selected from bromo (Br), chloro (Cl), fluro (F) and iodo (I).

The term "haloalkyl" as used herein refers to an alkyl group as defined above substituted with between one and three halogen atoms including, but not limited to, fluoromethyl, trifluoromethyl and fluoroethyl.

The term "acylated" as used herein refers to an alkyl group attached to a carbonyl.

The term "protecting group" as used herein is a term well-known in the art and refers to substituents on functional groups of compounds undergoing chemical transformation which prevent undesirable reactions and degradations during a synthesis; see, for example, T. H. Greene, "Protective Groups in Organic Synthesis", John Wiley and Sons (1981).

The term "N-protected" and "N-protecting" as used herein refer to the use of a group intended to protect an amino function or the N-terminus of an amino acid or peptide against undesirable reactions during a synthetic procedure or to prevent the attack of exopeptidases on the compound or to increase the solubility of the compound and includes, but is not limited to, such uses sulfonyl; acyl, such as acetyl, pivaloyl and benzoyl; alkoxycarbonyl, such as tertbutyloxycarbonyl (BOC), benzyloxycarbonyl (Cbz); and L- or D-aminoacyl residues, which may themselves be N-protected. Other examples may be found in 'The Peptides' E. Gross and J. Meinenhofer, Vol 3, Academic Press (1981).

It will be appreciated by those skilled in the art that the compounds of Formula II and Formula III, depending on the substituents, may contain one or more chiral centers and thus exist in the form of many different isomers, optical isomers (i.e. enantiomers) and mixtures thereof including racemic mixtures. All such isomers, enantiomers and mixtures thereof including racemic mixtures are included within the scope of the invention.

The compound of Formula I, Canadensol, has been isolated from the needles of the Taxus genus. The vegetal material preferably consists of the needles which is rapidly regenerated and therefore in abundant supply, though other material such as the roots or the bark of the Taxus bushes may be used.

Early attempts at the recovery of Canadensol from the chromatographic fractions containing it, consisted of numerous reverse phase HPLC steps resulting in low yields.

The compound of Formula I extracted by means of chlorinated solvents, for example dichlormethane, in admixture with alcohols such as methyl alcohol. The purification of Canadensol requires a purification through column chromatography, wherein silica gel is preferably used as the stationary phase. Solvent mixtures, consisting of an aliphatic hydrocarbon, for example, hexane with a chlorinated solvent, such as dichloromethane, together with a higher polarity solvent, such as ethyl acetate or acetone are used as eluents.

The preferred compounds of the present invention can also be synthesized using a new and unique combination of conventional preparative steps and recovery methods known to those skilled in the art of organic and bio-oragnic synthesis, while providing a new and unique combinations for the overall synthesis of each compound. Preferred synthetic routes for intermediates involved in the synthesis as well as the resulting taxane derivative compounds of the present invention follow. Successful preparation of these compounds is possible by way of several synthetic routes: two of which are outlined in Schemes I and II (demonstrated in Examles I and II, correspondingly).

Briefly, the semi-synthesis methods use baccatin III as starting material, which can be obtained from a number of its derivatives, one of the preferred derivatives is 10-deacctylbaccatin III. The conversion of 10-deacctylbaccatin III into baccatin III can be achieved according to the technique described in Denis J N, et al. J. Am. Chem. Soc., 110:5917 (1988). The conversion of baccatin III into taxol derivatives requires that the hydroxyl moiety at C-7 be protected prior to derivatization with the appropriate side chain at C-13. The appropriate side chains can be synthesized from alkyl cinnamate. See Denis J N, et al., J. Org. Chem. 55:1959 (1990) for an example of a suitable side chain synthesised from methyl cinnamate.

Scheme I

Step A:

Compound (i); baccatin III, is derivatized at C-7 by reacting with Compoud (ii); a suitable protecting group (X). It is necessary to protect the hydroxyl group at position 7 of baccatin III, to prevent coupling at C-7 and/or racemization at C-7 (through retro-aldol reaction). This can be achieved through the use of silyl chlorides (for example from triethyl, tri-isopropyl, t-butyldimethyl or t-butyldiphenyl) or alkyl chlorides (for example from benzyl chloride, methoxy-methyl chloride, allyl chloride or methoxy-ethyl chloride) or by the use of dihydroyran. The above reaction yield Compound (iii); a 7-protected baccatin III intermediate.

Step B:

The 7-protected baccatin III intermediate, Compound (iii), is then coupled at C-13 by the use of an appropriate acid, Compound (iv). The appropriate acid can be synthesized from alkyl cinnamate. The above coupling procedure generates a taxol derivative with a protecting group at C-7 as illustrated in Compound (v).

Step C:

This step achieves two functions: the protecting group at C-7 is removed, and the cyclized side chain at C-13 is opened-up and the side chain amine is acylated. This transformation, into Compound (vi), can be achieved through the use of an organic acid, followed by acylation using bicarbonate salts and an acyl chloride. In Compound (vi), $R_1$ is selected from the group consisting: $C_1$–$C_6$ alkyl including methyl, isopropyl, isopropenyl, propenyl, butyl, cyclopropyl, substituted alkyl including halo, di-(trihalomethyl)methyl, 3'-trihalo-n-propyl, or phenyl substituted with: one, 2 or 3 $C_1$–$C_4$ alkyl, $C_1$–$C_3$ alkoxy, halo, $C_1$–$C_3$ alkylthio, trifluormethyl, $C_2$–$C_6$ dialkylamino, hydroxy or nitro, 2-furyl, 2-thienyl; 1-napthyl, 2-napthyl, isopropoxy, isopropenoxy, propenoxy, cyclopropoxy, di-(trihalomethyl)methoxy, 3'-trihalo-n-propanoxy, dimethylamino, ethylamino, isopropylamino, propylamino, isopropenamino, imidazol, acetyl, hydroxycarbonyl, 2-(hydroxy)ethyl, 2-(methyl)-propyl, benzyl. Where $R_1$ is isopropyl, this scheme can yield 0.86% (See Example 1).

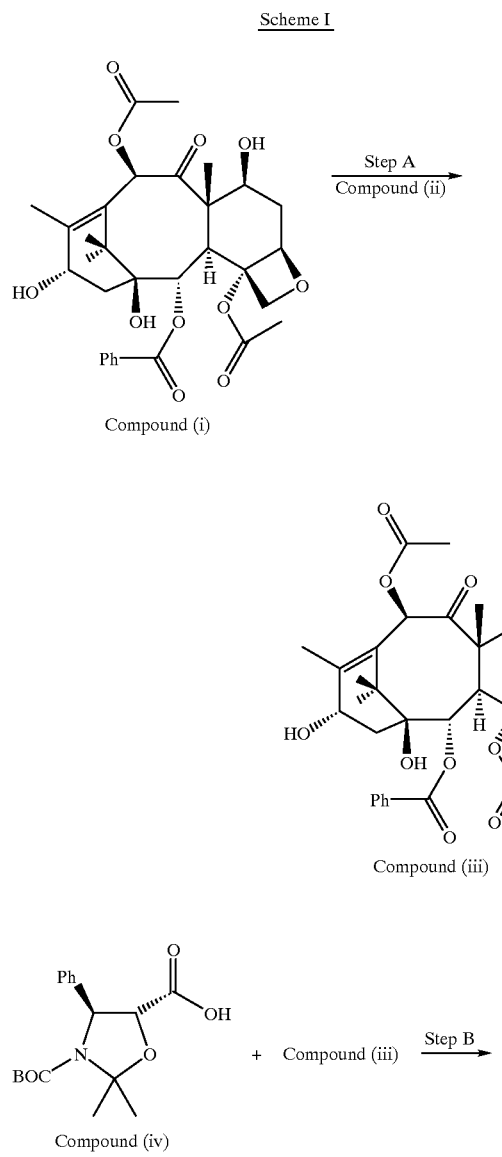

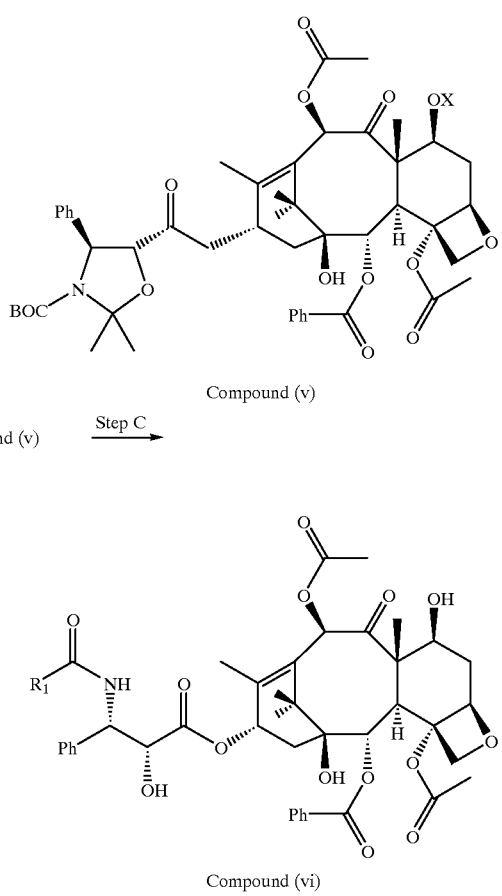

Scheme II

Step A:
Compound (i); baccatin III, is derivatized at C-7 by reacting with Compound (vii) a suitable protecting group (Y). It is necessary to protect the hydroxyl group at position 7 of baccatin III, to prevent coupling at C-7 and/or racemization at C-7 (through a retro-aldol reaction). This can be achieved through the use of chloroalkyl formates (for example from trichloroethyl chloroformate, trichloromethylchloroformate, dichloroethyl-chloroformate, dichloromethyl chloroformate, etc.). The above rection yields Compound (viii); a 7-protected baccatin III intermediate. When Y is —$CO_2CH_2CCl_3$, the yield of Compound (viii) is 25.5%.

Step B:
The 7-protected baccatin III intermediate, Compound (viii), is then coupled at C-13 by the use of the acid, Compound (iv) which can be synthesized from alkyl cinnamate. The above coupling procedure generates a taxol derivative with a protecting group at C-7 as illustrated in Compound (ix). When Y is —$CO_2CH_2CCl_3$, the coupling reaction with compound (iv) affords Compound (ix) in 53.3% yield.

Step C:
In Compound (x), $R_1$ is selected from the group consisting: $C_1$–$C_6$ alkyl including methyl, isopropyl, isopropenyl, propenyl, butyl, cyclopropyl, substituted alkyl including halo, di-(trihalomethyl)methyl, 3'-trihalo-n-propyl, or phenyl substituted with: one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, 2-furyl, 2-thienyl; 1-napthyl, 2-napthyl, isopropoxy, isopropenoxy, propenoxy, cyclopropoxy, di-(trihalomethyl)methoxy, 3'-trihalo-n-propanoxy, dimethylamino, ethylamino, isopropylamino, propylamino, isopropenamino, imidazol, acetyl, hydroxycarbonyl, 2-(hydroxy)ethyl, 2-(methyl)-propyl, benzyl.

In this step the cyclized side chain at C-13 is opened-up. This transformation, into Compound (x), can be achieved through the use of an organic acid, followed by alkylation using bicarbonate salts and an acyl chloride.

Step D:

The protecting group at C-7 is then removed from Compound (x) by the use of reducing agents such as zinc in the presence of acetic acid and methanol to yield Compound (vi). When $R_1$ is isopropyl, this scheme can yield 74.7% (See Example 2).

Scheme II

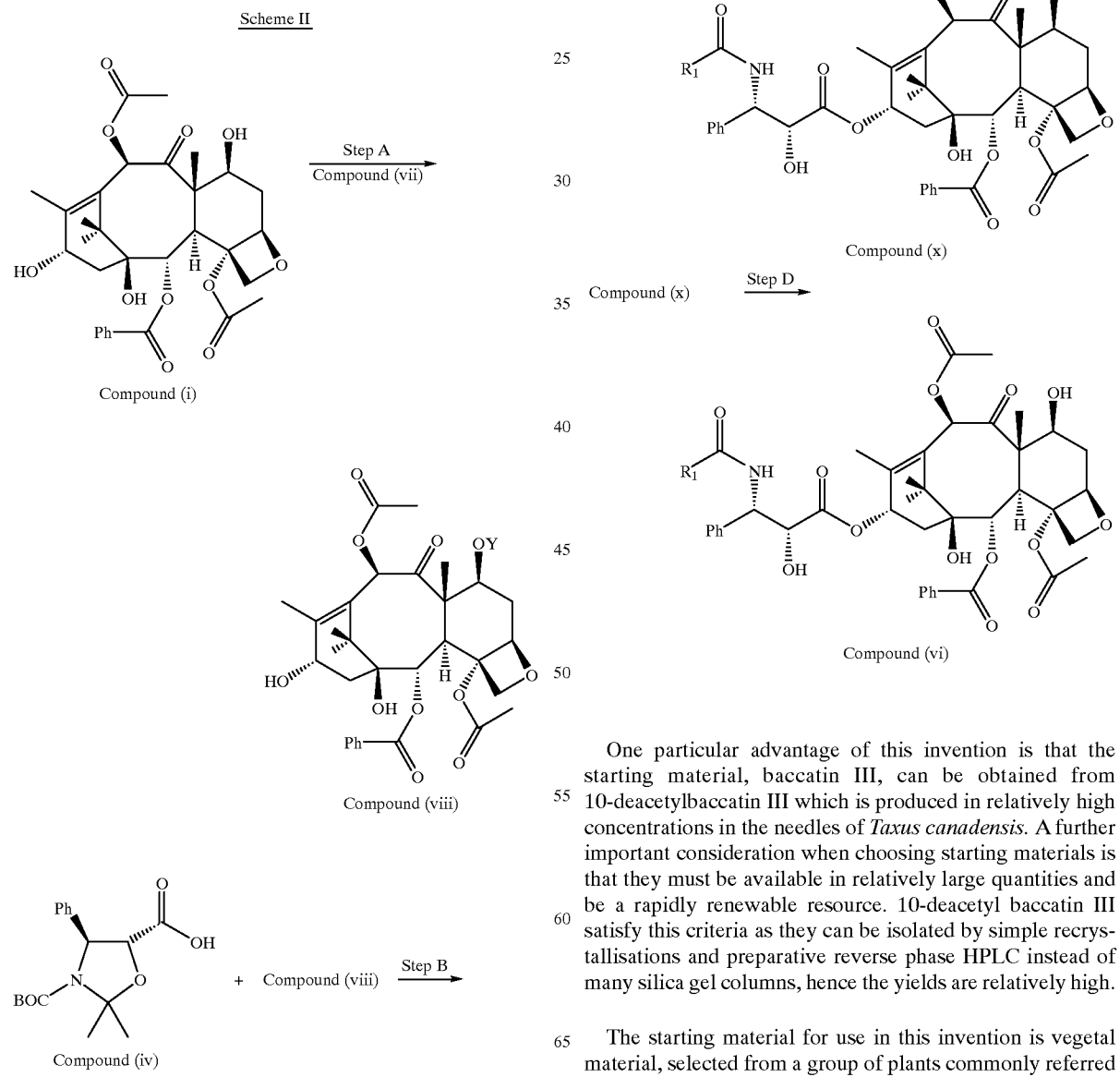

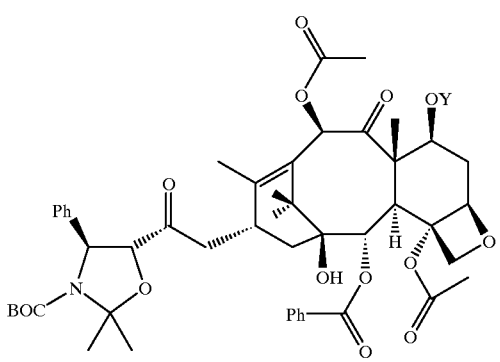

Compound (ix)

Compound (ix) →Step C→

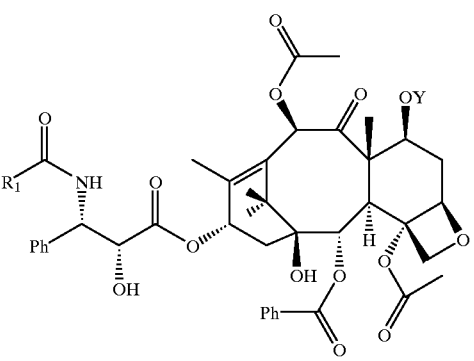

Compound (x)

Compound (x) →Step D→

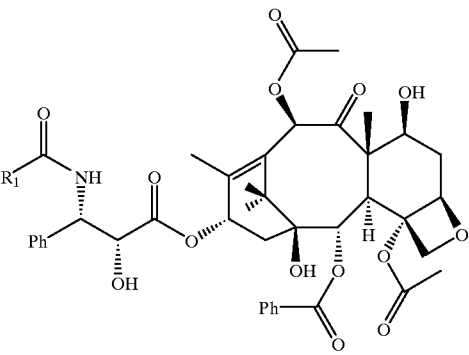

Compound (vi)

One particular advantage of this invention is that the starting material, baccatin III, can be obtained from 10-deacetylbaccatin III which is produced in relatively high concentrations in the needles of *Taxus canadensis*. A further important consideration when choosing starting materials is that they must be available in relatively large quantities and be a rapidly renewable resource. 10-deacetyl baccatin III satisfy this criteria as they can be isolated by simple recrystallisations and preparative reverse phase HPLC instead of many silica gel columns, hence the yields are relatively high.

The starting material for use in this invention is vegetal material, selected from a group of plants commonly referred to as taxads. The most suitable plant of this group are the species Taxus. The semi-synthetic method disclosed is effective when using the roots, bark or leaves of the Taxus plant but we consider it prudent to use a source that is rapidly regenerated (such as the leaves i.e. needles) and therefore in abundant supply. Amongst the Taxus species, *Taxus canadensis* is a preferred source for use in the semi-synthesis of the novel taxanes claimed in this invention. Thus one useful aspect of the current invention is largely dependent upon an abundant supply of baccatin III which can be derived from 10-deacetylbaccatin III.

Paclitaxel derivatives are useful for their antitumer activity, particularly for the treatment of the same cancers for which taxol has been shown active, including human lung tumors, melanoma, leukemia, mammary tumors, and colon cancer. We anticipate that the taxol derivatives of the current invention will have utility in the treatment of the same cancers for which taxol has been shown to be active.

Microtubules are an integral part of eukaryotic cells, and microtubule assembly is importantly associated with cell division and multiplication. Known antitumor compounds have been studied for their effect on microtubule assembly. For example, vinca alkaloids, such as vinblastine and vincristine have been shown to disrupt cellular microtubules, i.e. in vitro they have been shown to inhibit microtubule assembly and to depolymerize steady state microtubules. Similarly, colchicine has been shown to depolymerize microtubules in cells.

Paclitaxel has been shown to exhibit a very unique mechanism of action, in that it promotes the assembly of microtubules, but inhibits their disassembly, thereby interfering with the G2 and M phases of cell cycles and division. In vitro studies have shown that microtubules, once polymerized, in the presence of taxol reists depolymerization by other agents such as $CaCl_2$ or cold temperature which normally depolymerize microtubles.

The present inventors have conducted studies to investigate the effect of derivatives of taxol on the microtubule assembly. The microtubule assembly study was conducted using Canadensol according to the in vitro procedures disclosed, for example in Pamess et al., J. Cell Biol. 91:479 1981. In these studies, conditions can be established whereby a dynamic steady staet exists between tubulin assembling into microtubules and the disassembly at the other end. This dynamic steady staet can be measured spectrophotometrically, observing the absorbance of the solution at 350 nm. As stated above, it has been shown that taxol binds specifically and reversibly to the protein, stabilizing the microtubules in the polymerized form. This effect can be visualized by following the increase in absorbance of the solution at 350 nm. Cells treated with taxol, or derivative thereof which exhibit chemotherpeutic activity, usually die as they are effectively blocked in mitosis.

The results presented in FIGS. 1–4, indicate that compounds of Formula II (eg. when $R_1$ is isopropyl or propyl) exhibit excellent tubulin stabilizing activity. These compounds, therefore, are useful antitumor agents due to their biological activity. It is therefore one embodiment of the present invention to claim the use of the two compounds of Formula II, when $R_1$ is isopropyl and propyl, as anticancer agents.

The present invention also provides pharmaceutical compositions containing a compounds as disclosed in the claims in combination with one or more pharmaceutically acceptable, inert or physiologically active, diluents or adjuvants. The compounds of the invention can be freeze dried and, if desired, combined with other pharmaceutically acceptable excipients to prepare formulations for administration. These compositions may be presented in any form appropriate for the administration route envisaged. The parenteral and the intravenous route are the preferential routes for administration.

Compounds of the general Formula II may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula II and a pharmaceutically acceptable carrier. One or more compounds of general Formula II may be present in association with one or more non-toxic pharmaceutically acceptable carriers and/or diluents and/or adjuvants and if desired other active ingredients. The pharmaceutical compositions containing compounds of general Formula II may be in a form suitable for oral use, for example, as tablets, troches, lozenges, aqueous or oily suspensions, dispersible powders or granules, emulsion hard or soft capsules, or syrups or elixirs.

Compositions intended for oral use may be prepared according to any known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptably excipients which are suitable for the manufacture of tablets. These excipients may be for example, inert diluens, such as calcium carbonate, sodium carbonate, lactose, calcium phosphate or sodium phosphate: granulating and disintegrating agents for example, corn starch, or alginic acid: binding agents, for example starch, gelatin or acacia, and lubricating agents, for example magnesium stearate, stearic acid or talc. The tablets may be uncoated or they may be coated by known tecniques to delay disintegration and aborption in the gastorintestinal tract and thereby provide a sustained action over a longer period. For example, a time delay material such as glyceryl monosterate or glyceryl distearate may be employed.

Formulations for oral use may also be presented as hard gelatign capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain active materials in admixture with excipients suitable for the manufacture of aqueous suspensions. Such excipients are suspending agents, for example sodium carboymethylcellulose, methyl cellulose, hydropropylmethylcellulose, sodium alginate, polyvinylpyrrolidone, gum tragacanth and gum acacia: dispersing or wetting agents may be a naturally-occurring phosphatide, for example, lecithin, or condensation products of an alkylene oxide with fatty acids, for example polyoxyethyene stearate, or condensation products of ethylene oxide with long chain aliphatic alcohols, for example heptadecaethyleneoxycetanol, or condensation produces of ethylene oxide with partial esters derived from fatty acids and a hexitol such as polyoxyethylene sorbitol monooleate, or condensation products of ethylene oxide with partial esters derived from fatty acids and hexital anhydrides, for example polyethylene sorbitan monooleate. The aqueous suspensions may also contain one or more preservatives, for example ethyl, or n-propyl p-hydroxy-benzoate, one or more coloring agents, one or more flavoring agents or one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening flavoring and coloring agents, may also be present.

Pharmaceutical compositions of the invention may also be in the form of oil-in-water emulsions. The oils phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulation according to known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water. Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compound(s) of the general Formula I, Formula II and Formula III may be administered, together or separately, in the form of suppositories for rectal administration of the drug. These compositions can be prepared by mixing the drug with a suitable non-iritating excipient which is solid at ordinary temperatures but liquid at the rectal temperature and will therefore melt in the rectum to release the drug. Such materials are cocoa butter and polyethylene glycols.

Compound(s) of general Formula I, Formula II, and Formula III may be administered, together or separately, parenterally in sterile medium. The drug, depending on the vehicle and concentration used, can either be suspended or dissolved in the vehicle. Advantageously, adjuvants such as local anaesthetics, preservatives and buffering agents can be dissolved in the vehicle.

The mode, dosage and schedule of administration of taxol in human cancer patients has been studied extensively (see Ann. Int. Med. 111:273 1989). For the compounds of this invention, the dose to be administered, whether a single dose, multiple does, or a daily dose, will vary with the particular compound being used. Factors to consider when deciding upon a dose regimen include potency of the compound, route of administration, size of the recipient and the nature of the patient's condition.

The dosage to be administered is not subject to defined limits, but in will usually be an effective amount. It will usually be the equivalent, on a molar basis of the pharmacologically active free form produced from a dosage formulation upon the metabolic release of the active free drug to achieve its desired pharmacological and physiological effects.

An oncologist skilled in the art of cancer treatment will be able to ascertain, without undue experiments, appropriate protocols for effective administration of the compounds of this present invention by referring to the earlier studies of taxol and its derivatives.

Particular reagents and conditions utilized in these syntheses are described in detail in the Examples which follow. Also, it will be appreciated by one skilled in the art that selective protection and deprotection steps affecting the several hydroxyl groups on the baccatin III structure may be carried out in varying order or number of steps, as necessary, and that Schemes I and II are intended to encompass such variations.

The *Taxus canadensis* plant was extracted as reported previously (L. O. Zamir, M. E. Nedea, Z.-H. Zhou, S. Bélair, G. Caron, F. Sauriol, E. Jacqmain, F. I. Jean, F.-X. Garneau and O. Mamer, Can. J. Chem. 73:655, 1995), the additional chromatographic purification step leading to a new taxane with a side chain, never isolated before in Taxus spp. is described below.

Isolation of Taxanes with Reverse Phase HPLC: Taxanes in the brown solid are separated on a preparative HPLC using an ODS-2 reverse phase column (2.0×50 cm; Whatman) and a Waters Delta Prep 3000 instrument coupled to a model 481 variable wavelength detector at 227 nm. The products are eluted with a gradient over 140 minutes of acetonitrile:water (25:75) to 100% acetonitrile. At 55.5 min, a peak comprising 10 hydroxyacetylbaccatin VI, among other taxanes is collected.

Isolation of N-debenzoyl-N-n-pentanoylpaclitaxel with Reverse Phase HPLC: The peak at 55.5 minutes was found to contain the compound N-debenzoyl-N-n-pentanoylpaclitaxel. In order to isolate this compound, the 55.5 minute peak was separated further utilizing the same preparative HPLC system as described above. However, this separation used a gradient over 50 minutes of isopropanol:water (25:75) to 100% isopropanol at a flow rate of 6 mL per minute. The largest peak from the gradient was centerd at a retention time of 41 minutes. The shoulder of this 41 minute-centered peak, from 44 to 48 minutes, was collected and purified further using the same HPLC system eluting with a gradient over 100 minutes of isopropanol:water (25:75) to 100% isopropanol at a flow rate of 7 mL per minute. The product eluting at 55 minutes was collected. Analysis of the product on analytical HPLC yielded a single pure product eluting at 32.9 minutes when using a gradient over 50 minutes of acetonitrile:water (25:75) to 100% acetonitrile. The structure of N-debenzoyl-N-n-pentanoylpaclitaxel was elucidated by NMR analysis, the results being listed in FIG. 5.

Further, to assist in understanding the current invention, the following non-limiting examples are provided. The following examples should not be construed as specifically limiting the present invention, variations presently known or later developed, which would be in the understanding of one skilled in the art and considered to fall within the scope of the present invention as described herein.

EXAMPLE 1

Semi-Synthesis of Canadensol (Scheme I)

The preparation of Compound 1 was carried out through eight step reactions from methyl cinnamate (as described in Denis J. D., Correa A., Greene A. E., J. Org. Chem., 55:1959, 1990). The preparation of Compound 2 was carried out through two step reactions from 10-deacetyl baccatin III (as described in Denis J. N., Greene A. E., Guenard D., Gueritte-Voegelelein F., Mangatal L., Potier P. J., Am. Chem. Soc., 110:5917, 1988).

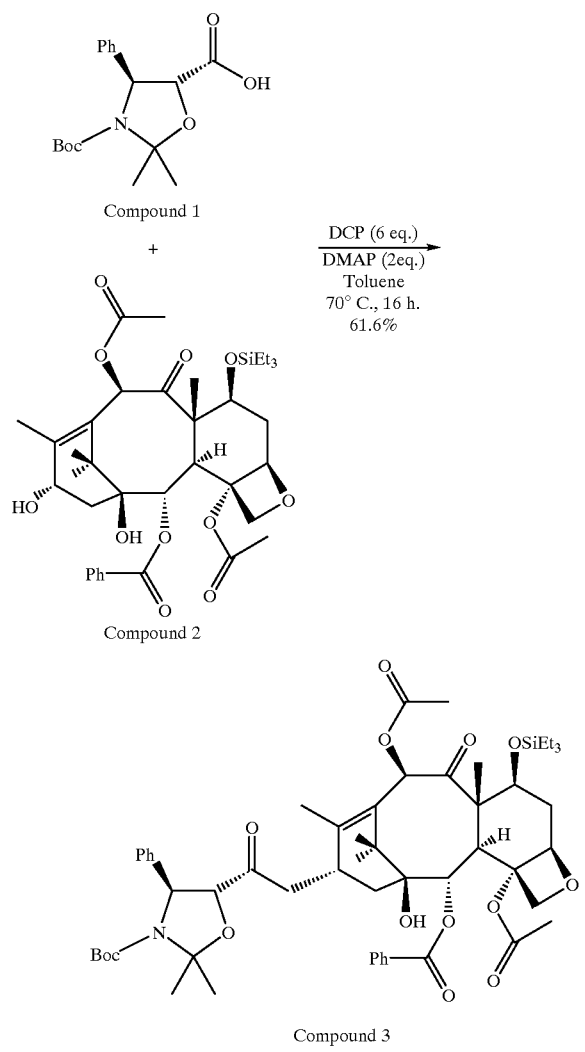

The reaction conditions for the preparation of Compound 3 were determined experimentally to be as follows. A solution of Compound 1 (32.8 mg, 0.102 mmol) and di-2-pyridyl carbonate (DPC, 22.2 mg, 0.102 mmol) in dry toluene (3.0 mL) was stirred at room temperature under nitrogen for 15 mins. Dimethylaminopyridine (DMAP, 4.2 mg, 0.034 mmol) and 7-triethyl silyl-10-deacetyl baccatin III (Compound 2) (12.0 mg, 0.017 mmol) was added to the mixture. The reaction mixture was heated at 72° C. for 16 hours, then allowed to cool to room temperature. The organic solvent was removed by rotary evaporation. The crude product was dissolved in methanol (1.0 mL) and filtered. The solution of crude product was purified by preparative reverse phase HPLC (50 cm) using linear gradient of acetonitrile (25% to 100%) in water over 70 minutes to give pure Compound 3 ($R_t$=77.6 min) as a white solid (10.5 mg, 61.6% yield, $R_f$ 32 0.51, EtOAc/Hexane=3/7). Analytical HPLC using linear gradient of acetonitrile (25% to 100%) in water over 50 minutes for Compound 3 gave retention time ($R_t$=62.8 min). HRMS:MH$^+$ requires: 1004.48277, Found 1004.48280; $^1$H-NMR of Compound 3: (500 MHz, CDCl$_3$) δ 8.04 (d, J=7.3 Hz, 2H), 7.63 (t, J=7.3 Hz, 1H), 7.49 (t, J=7.8 Hz, 2H), 7.40–7.30 (m, 5H, 3'-Ph), 6.44 (s, 1H, H-10), 6.23 (t, J=8.3 Hz, 1H, H-13), 5.65 (d, J=6.8 Hz, 1H, H-2), 5.04 (br., 1H, H-3'), 4.87 (d, J=8.8 Hz, 1H, H-5), 4.46 (d, J=6.3 Hz, 1H, H-2'), 4.44 (o.m, 1H, H-7), 4.24 (d, J=8.3 Hz, 1H, H-20a), 4.10 (d, J=8.3 Hz, 1H, H-20b), 3.77 (d, J=6.8 Hz, 1H, H-3), 2.49 (ddd, J=14.6, 9.8, 6.3 Hz, 1H, H-6a), 2.20 (s, 3H, OAc), 2.15 (d, J=9.3 Hz, 2H, H-14), 2.04 (s, 3H, Me-18), 1.87 (s, 3H, OAc), 1.82 (o.m, 1H, H-6b), 1.65 (s, 3H Me-19), 1.60 (br, t-Bu), 1.22 (s, 3H, Me-16 or 17), 1.20 (s, 3H, Me-17 or 16), 1.11 (br, t-Bu), 0.57 (s, 6H, Si—CH$_2$), 0.91 (t, J=7.8 Hz, 9H, Si—CH$_2$Me). This reaction was repeated another two times at the same scale. The yield of the later two reactions were 51.2% and 68.0%. Thus, the yield of this reaction varies from 51.2%–68.0%

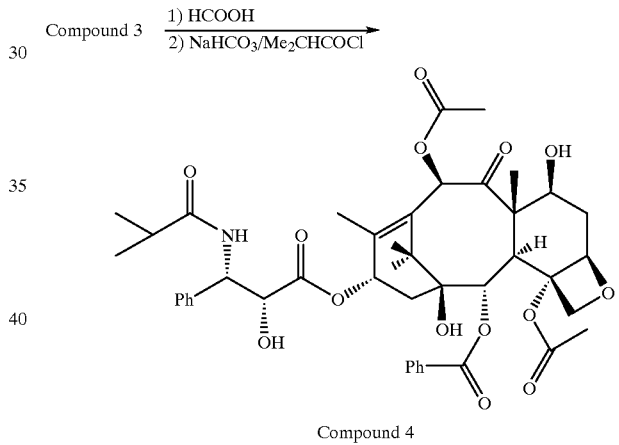

Compound 3 (4.0 mg, 0.004 mmol) was stirred in 0.3 mL of 95–97% formic acid at room temperature for 4 hours. The formic acid was then removed by a flow of nitrogen and the crude product was dried under vacuum. The residue was dissolved in EtOAc (0.5 mL), and then NaHCO$_3$ (10.0 mg) and isobutyryl chloride (5 μL, 0.047 mmol) were added. After stirring for 1 hour, EtOAc (10 mL) was added to the solution. The organic phase was washed with brine (3.0 mL) and dried over anhydrous MgSO$_4$. After filtration and evaporation, the residue was purified by preparative HPLC ($R_t$=35.9 mins, acetonitrile from 25% to 100% in water over 70 minutes). Compound 4 (Canadensol) was obtained as a white solid (46 μg, 1.4% yield based on Compound 3). Analytical HPLC using linear gradient of acetonitrile (25% to 100%) in water over 50 minutes for Compound 4 gave retention time of 32.19 mins. HRMS: MH$^+$ requires: 820.35423, Found: 820.35443; $^1$H-NMR of combined samples of Compound 4: (500 MHz, CDCl$_3$) δ 8.11 (d, J=7.8 Hz, 2H) 7.60 (t, J=7.3 Hz, 1H), 7.5 (t, J=7.6 Hz, 2H), 7.40–7.30 (m, 5H, 3'-Ph), 6.27 (s, 1H, H-10), 6.20 (t, J=9.5 Hz, 1H, H-13), 5.67 (d, J=6.5 Hz, 1H, H-2), 5.57 (d, J=8.8

Hz, 1H, H-3'), 4.93 (d, J=9.1 Hz, 1H, H-5), 4.68 (o.m, 1H, H-2'), 4.39 (o.m, 1H, H-7), 4.24 (d, J=8.8 Hz, 1H, H-20a), 4.18 (d, J=8.8 Hz, 1H, H-20b), 3.78 (d, J=6.8 Hz, 1H, H-3), 3.40 (d, J=5.1 Hz, 1H, 2'-OH), 2.53 (ddd, J=15.4, 8.1, 7.2 Hz, 1H, H-6a), 2.38 (o.m, 1H, Me$_2$CHCONH), 2.35 (s, 3H, OAc), 2.28 (o.m, 2H, H-14), 2.24 (s, 3H, OAc), 1.84 (o.m, 1H, 6b), 1.81 (s, 3H, Me-18), 1.67 (s, 3H, Me-19), 1.26 (s, 3H, Me-16 or 17), 1.15 (s, 3H, Me-17 or 16), 1.11 (2d, J=6.5, 6.1 Hz, 6H Me$_2$CHCONH). This reaction was repeated two times. The yield of the later reaction was 1.8% and 12.8%. Thus the yield of this reaction varies from 1.4%–12.4%.

EXAMPLE 2

Semi-synthesis of Canadensol and a Structural Analogue

The preparation of Compound 1 was carried out through eight step reactions from methyl cinnamate (as described in Denis J. D., Correa A., Greene A. E., J. Org. Chem., 55:1959, 1990). The preparation of Coupound 5 was carried out through three step reactions from 10-deacetylbaccatin III (as described in Denis J. N., Greene A. E., Guenard D., Gueritte-Vocgelelein F., Mangatal L., Potier P. J., Am. Chem. Soc., 110:5917, 1988). The reaction conditions for the preparation of Compound 6 were determined experimentally to be as follows:

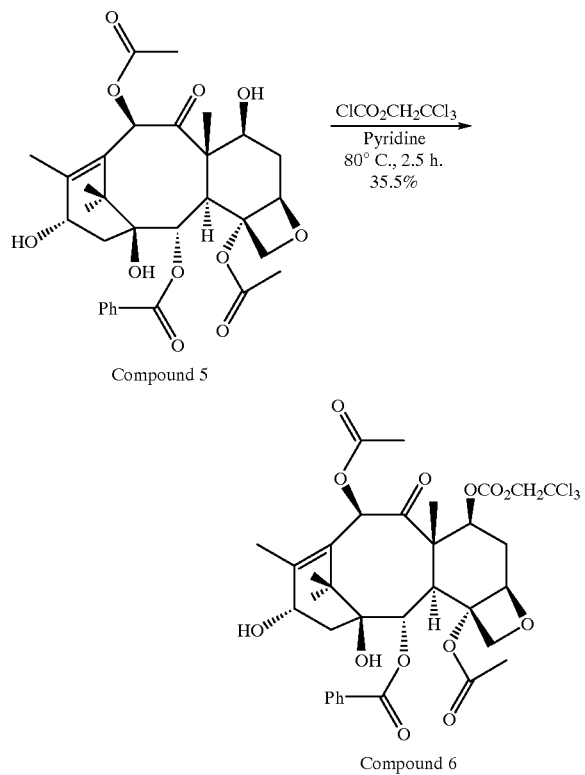

Compound 5

Compound 6

To a solution of Compound 5 (baccatin III) (78 mg, 0.133 mmol) in pyridine (1.5 mL) was added 2,2,2-trichloroethylchloroformate (62 μL; 0.452 mmol) at 80° C. This mixture was stirred at 80° C. for 2.5 hours. Water (5 mL) was added and most of the pyridine was evaporated. The aqueous phase was extracted with CH$_2$Cl$_2$ (3×20 mL). The organic phase was dried over MgSO$_4$ and evaporated. The crude product was dissolved in methanol (2.0 mL) and filtered. the solution of crude product was purified by preparative HPLC using linear gradient of acetonitrile (25% to 100%) in water over 70 minutes to give pure Compound 6 (R$_t$ 52.0 min) as a white solid (36 mg, 25.5% yield, R$_f$=0.38, EtOAc/CH$_2$Cl$_2$=1/4) and recovery of Compound 5 (baccatin III). Analytical HPLC using linear gradient of acetonitrile (25% to 100%) in water over 50 minutes for Compound 6 gave a retention time of 44.0 mins. $^1$H-NMR of Compound 6: (500 MHz, CDCl$_3$) δ 8.09 (d, J=7.6 Hz, 2H) 7.61 (t, J=7.2 Hz, 1H), 7.48 (t, J=7.6 Hz, 2H), 6.38 (s, 1H, H-10), 5.62 (d, J=7.5 Hz, 1H, H-2), 5.58 (m, 1H, H-7), 5.02 and 4.63 (2d, J=12.5 Hz, 2H, CH$_2$CCl$_3$), 4.97 (d, J=9.3 Hz, 1H, H-5), 4.87 (m, 1H, H-13), 4.32 (d, J=8.6 Hz, 1H, H-20a), 4.14 (d, J=8.6 Hz, 1H, H-20b), 4.01 (d, J=6.8 Hz, 1H, H-3), 2.63 (ddd, J=15.0, 8.5, 7.0 Hz, 1H, H-6a), 2.29 (s, 3H, OAc), 2.15 (d, J=9.3 Hz, 2H, H-14), 2.04 (s, 3H, Me-18), 2.03 (m, 1H, H-6b) 1.82 (s, 3H, OAc), 1.58 (s, 3H, Me-19), 1.13 (s, 3H, Me-16 or 17), 1.09 (s, 3H, Me-17 or 16).

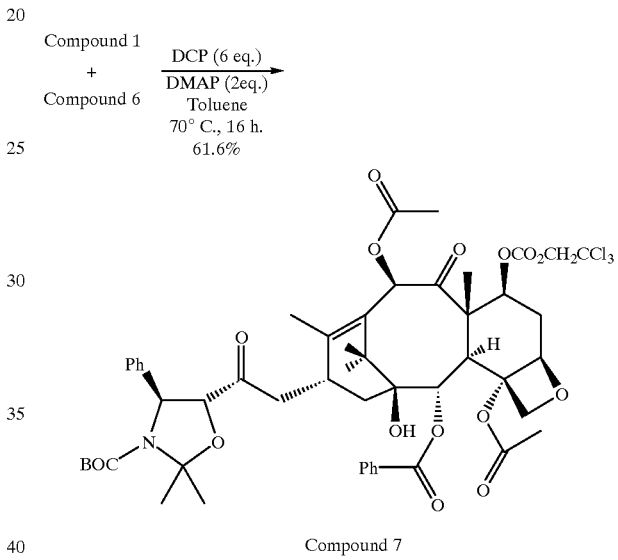

Compound 7

The reaction conditions for the preparation of Compound 7 were determined experimentally to be as follows: A solution of Compound 1 (90.8 mg; 0.282 mmol) and di-2-pyridyl carbonate (DPC, 61.3 mg; 0.828 mmol) in dry toluene (5.0 mL) was stirred at room temperature under nitrogen for 15 minutes. Dimethylaminopyridine (DMAP, 11.7 mg; 0.0954 mmol) and 7-(2,2,2-trichloroethyl-oxycarbonyl)-baccatin III (Compound 6) (36.3 mg; 0.0476 mmol) was added to the mixture and stirred at 72° C. for 6 hours. The organic solvent was removed by rotary evaporation. The crude product was dissolved in methanol (1.5 mL) and filtered. The solution of crude product was purified by preparative HPLC using linear gradient of acetonitrile (25% to 100%) in water over 70 minutes to give pure Compound 7 (R$_t$=77.3 min) as a white solid (27.0 mg; 53.3% yield; R$_f$=0.43, EtOAc/hexane=1/1). Analytical HPLC using linear gradient of acetonitrile (25% to 100%) in water over 50 minutes for Compound 7 gave retention time (R$_t$=56.2 min). $^1$H-NMR of Compound 7: (500 MHz, CDCl$_3$) δ 8.04 (d, J=7.3 Hz, 2H), 7.64 (t, J=7.3 Hz, 1H), 7.50 (t, J=7.8 Hz, 2H), 7.40–7.30 (m, 5H, 3'-Ph), 6.36 (s, 1H, H-10), 6.26 (br.t, J=8.5 Hz, 1H, H-13), 5.65 (d, J-7.1 Hz, 1H, H-2), 5.58 (dd, J=10.7, 7.1 Hz, 1H, H-7), 5.04 (br., 1H, H-3'), 5.03 and 4.64 (2d, J=12.0 Hz, 2H, CH$_2$CCl$_3$), 4.91

(dd, J=9.7, 1.5 Hz, 1H, H-5), 4.47 (d, J=6.9 Hz, 1H, H-2'), 4.27 (d, J=8.5 Hz, 1H, H-20a), 4.11 (d, J=8.5 Hz, 1H, H-20b), 3.93 (d, J=7.1 Hz, 1H, H-3), 2.59, (ddd, J=14.6, 9.7, 7.1 Hz, 1H, H-6a), 2.18 (om, 2H, H-14), 2.17 (s, 6H, 2OAc), 2.03 (o.m, 1H, H-6b), 2.00 (d, J=1.0 Hz, 3H, Me-18), 1.91 and 1.80 (2s, 6H, Me$_2$CNO), 1.76 (s, 3H Me-19), 1.24 (s, 3H, Me-16 or 17), 1.16 (s, 3H, Me-17 or 16), 1.10 (br, t-Bu).

Compound 7 $\xrightarrow[\text{2) NaHCO}_3/\text{Me}_2\text{CHCOCl}]{\text{1) HCOOH}}$ 50%

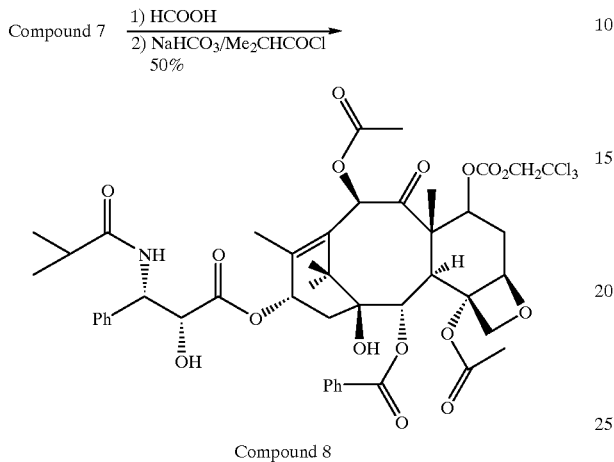

Compound 8

The reaction conditions for the preparation of Compound 8 were determined experimentally to be as follows: Compound 7 (26.0 mg; 0.0244 mmol) was stirred in formic acid (2.0 mL) at room temperature for 4 hours. Formic acid was then removed by a flow of nitrogen and crude product was obtained under vacuum. The residue was redissolved in EtOAc (3.0 mL). Then, NaHCO$_3$ (61 mg; 0.726 mmol) and isobutyryl chloride (26 µL; 0.0366 mmol) were added. After being stirred for 1 hour EtOAc (20 mL) was added to the mixture. The organic phase was washed with a saturated solution of NaCl (5 mL) and dried over MgSO$_4$. After filtration and evaporation, the residue was purified by preparative HPLC using linear gradient of acetonitrile (25% to 100%) in water over 70 minutes to give pure Compound 8 (R$_t$=55.8 min) as a white solid (12.0 mg; 50.0% yield; R$_f$=0.19; EtOAc/Hexane=1/1). Analytical HPLC using linear gradient of acetonitrile (25% to 100%) in water over 50 mins for Compound 8 gave retention time (R$_t$=46.1 min). $^1$H-NMR of Compound 8: (500 MHz, CDCl$_3$) δ 8.10 (d, J=7.8 Hz, 2H), 7.62 (t, J=7.3 Hz, 1H), 7.51 (t, J=7.6 Hz, 2H), 7.43–7.34 (m, 5H, 3'-Ph), 6.35 (s, 1H, H-10), 6.26 (d, J=9.1 Hz, 1H, NH-4'), 6.16 (br.td, J=9.0, 1.3 Hz, 1H, H-13), 5.69 (d, J=7.1 Hz, 1H, H-5), 5.58 (dd, J=9.0, 2.4 lHz, 1H, H-3'), 5.54 (dd, J=10.5, 7.3 Hz, 1H, H-7), 5.03 and 4.64 (2d, J=12.0, 12.0 Hz, 2H, CH$_2$CCl$_3$), 4.95 (br.d, J=9.5 Hz, 1H, H-5), 4.70 (dd, J=4.8, 2.4 Hz, 1H, H-2'), 4.31, (d, J=8.6 Hz, 1H, H-20a), 4.18 (d, J=8.5 Hz, 1H, H-20b), 3.92 (d, J=7.0 Hz, 1H, H-3), 3.42 (d, J=4.9 Hz, 1H, OH-2'), 2.61 (ddd, J=14.4, 9.8, 7.1 Hz, 1H, H-6a), 2.40 (o.septet, J=6.8 Hz, 1H, Me$_2$CHCONH), 2.36 (s, 3H, OAc), 2.33 (dd, J=9.0, 1.4 Hz, 2H, H-14), 2.17 (s, 3H, OAc), 2.05 (m, 1H, H-6b), 1.88 (s, 3H, Mc-18), 1.84 (s, 3H, Me-19), 1.24 (s, 3H Me-16 or 17), 1.18 (s, 3H, Me-17 or 16), 1.13 and 1.12 (2d, J=6.8, 6.8 Hz, 6H, Me$_2$CHCONH).

Compound 8 $\xrightarrow{\text{Zn/MeOH/MeCOOH}}_{60°\text{C., 1 h., 74.7\%}}$

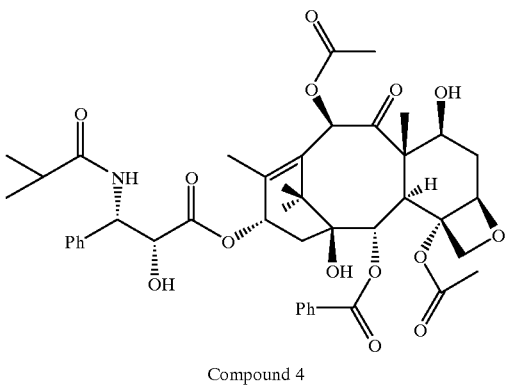

Compound 4

The reaction conditions for the preparation of Compound 4 were determined experimentally to be as follows: To a solution of Compound 8 (11.7 mg; 0.0117 mmol) in acetic acid:methanol (1:1, v/v, 2 mL) was added zinc powder (70.6 mg) at 60° C. under nitrogen. This mixture was stirred at 60° C. under nitrogen for 1 hour. Then CH$_2$Cl$_2$ (20 mL) was added and the mixture was filtered through celite. The organic solvent was evaporated to give crude product. The residue was purified by preparative HPLC using linear gradient of acetonitrile (25% to 100%) in water over 70 minutes to give pure Compound 4 (R$_t$=37.0 min) as a white solid (7.2 mg; 74.7% yield). Analytical HPLC using linear gradient of acetonitrile (25% to 100%) in water over 50 minutes for Compound 4 gave retention time (R$_t$=33.0 min). HRMS: MH$^+$ requires: 820.35423, Found: 820.35443; $^1$H-NMR of Compound 4: (500 MHz, CDCl$_3$) δ 8.12 (d, J=6.8 Hz, 2H) 7.61 (t, J=7.3 Hz, 1H), 7.51 (t, J=7.6 Hz, 2H), 7.44–7.30 (m, 5H, 3'-Ph), 6.28 (s, 1H, H-10), 6.24 (d, J=9.0 Hz, 1h NH-4'), 6.20 (t, J=8.5 Hz, 1H, H-13), 5.68 (d, J=7.1 Hz, 1H, H-2), 5.57 (d, J=9.0, 2.5 Hz, 1H, H-3'), 4.94 (dd, J=9.8, 2.2 Hz, 1H, H-5), 4.69 (d, J=2.7 Hz, 1H, H-2'), 4.40 (dd, J=11.2, 5.8 Hz, 1H, H-7), 4.29 (d, J=8.5 Hz, 1H, H-20a), 4.19 (d, J=8.5 Hz, 1H, H-20b), 3.78 (d, J=7.1 Hz, 1H, H-3), 2.54 (ddd, J=14.9, 9.8, 6.9 Hz, 1H, H-6a), 2.39 (o.septet, J=6.8 Hz, 1H, Me$_2$CHCONH), 2.35 (s, 3H, OAc), 2.28–2.32 (m, 2H, H-14), 2.24 (s, 3H, OAc), 1.88 (ddd, J=13.4, 11.0, 2.2 Hz, 1H, H-6b), 1.82 (s, 3H, Me-18), 1.68 (s, 3H, Me-19), 1.26 (s, 3H, Me-16 or 17), 1.15 (s, 3H, Me-17 or 16), 1.12 and 1.11 (2d, J=7.0, 6.8 Hz, 6H Me$_2$CHCONH).

EXAMPLE 3

Semi-synthesis of N-debenzoyl-N-n-pentanoyl-paclitaxel

Following the same method of synthesis as described in Example 2, alternatively, Compound 7 can be transformed into a family of related taxanes by the use of different alkyl chlorides. Specifically, Compound 7 can be transformed into a family of related taxanes by the use of different acyl chlorides, for example:

Compound 7 (12 mg; 0.011 mmol) was stirred in formic acid (0.5 mL) at room temperature for 4 hours and the solution was then evaporated with a stream of nitrogen. Ethyl acetate (1.5 mL), sodium bicarbonate (15 mg; 0.18 mmol) and propanoyl chloride (14.5 µL; 0.12 mmol) were added and the mixture stirred for 1 hour at room temperature. Ethyl acetate (20 mL) was added and the solution was washed with saturated sodium chloride, dried over anhydrous magnesium sulphate and evaporated. The residue was purified on preparative HPLC using a linear gradient of acetonitrile (25% to 100% ) in water over 70 minutes to yield Compound 9 (Rt=57.5 min) as a white solid (8.5 mg; 77% yield). Analytical HPLC using a linear gradient of acetonitrile (25% to 100%) in water over 50 min for Compound 9 gave a retention time of 47.3 min.

Compound 7 $\xrightarrow[\substack{2) \text{ NaHCO}_3/ \\ \text{CH}_3\text{CH}_2\text{CHCOCl} \\ 77\%}]{1) \text{ HCOOH}}$

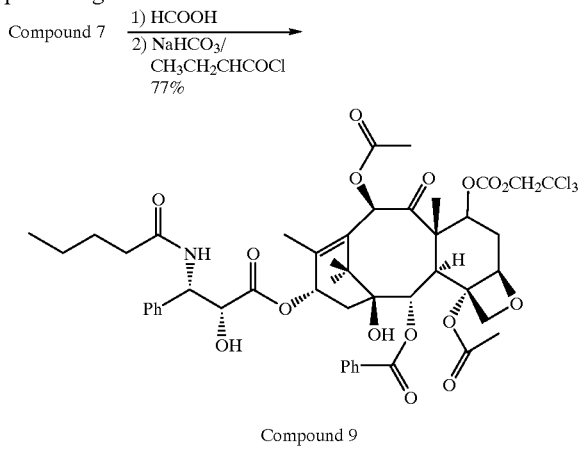

Compound 9

Compound 9 (7.0 mg; 0.0072 mmol) was dissolved in 3.0 mL of a solution of methanol:acetic acid (1:1, v/v) and zinc (30.0 mg; 0.46 mmol) was added. The mixture was stirred at 60° C. for 1 hour. The mixture was then left to cool at room temperature and then dichloromethane (20 mL) was added. Filtration over celite and purification on preparative HPLC using a linear gradient of acetonitrile (25% to 100%) in water over 70 minutes (Rt=42.5 min) afforded Compound 10 as a white solid (2.6 mg; 44% yield).

Compound 9 $\xrightarrow[\substack{60° \text{ C., 1 h.,} \\ 44\%}]{\text{Zn/MeOH/MeCOOH}}$

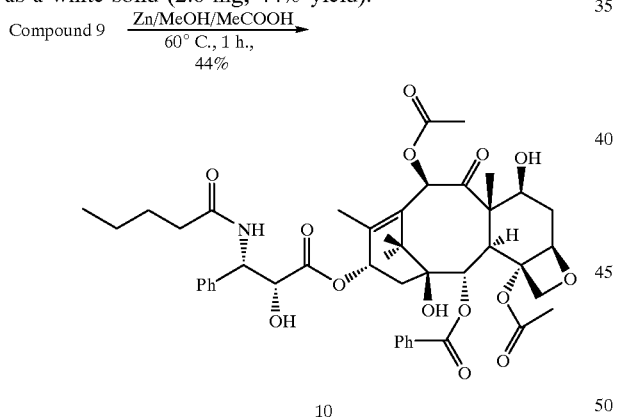

10

Analytical HPLC using a linear gradient of acetonitrile (25% to 100%) in water over 50 minutes for Compound 10 gave a retention time of 34.8 min. HRMS with KI as an internal standard: expected molecular weight; 872.32596 obtained 872.32574.

EXAMPLE 4

Semi-Synthesis of Canadensol (Scheme III)

The semi-synthesis of canadensol, taxcultine or any of the other biological active compounds can be obtained using baccatin III as starting material. The conversion of the natural product 10-deacetylbaccatin III into baccatin III can be achieved according to the technique described in Denis J. N. et al., J. Am. Chem. Soc., 110: 5917 (1988). The conversion of baccatin III into canadensol requires that the hydroxyl at C-7 be protected prior to derivatization with the appropriate side chain at C-13. An appropriate side chain is the triethylsilyl derivative of the C-7 hydroxyl). For the supply of large amounts of canadensol, taxcultine, etc, the addition of the side chains at C-13 is achieved in higher yields with the use of a range of side chains by Ojima's method (Ojima, I. et al., Tetrahedron, 48. 6985–7012, 1992; and Ojima, I. et al., Tetrahedron Letters, 34, 4149–4152, 1992).

The β-lactam (1) was obtained from (3R,4S)-3-hydroxy-4-phenylazetidin-2-one (which was prepared according to Ojima, I. et al Tetrahedron, 48, 6985–7012, 1992) by treatment with tetrabutyl ammonium fluoride according to the following conditions: (3R,4S)-3-isopropylsilyoxy-4-phenylazetidin-2-one (0.200 g; 0.626 mmol) was dissolved in dry tetrahydrofuran (4 mL) under nitrogen at room temperature. To this was added a solution of a n-Bu$_4$N$^+$F$^-$ (1.0M in dry tetrahydrofuran; 1.2 ml; 1.2 mmol; 1.9 eq.) and stirred for 2.5 hours at room temperature. The reaction was complete as shown by thin layer chromatography with 35% ethylacetate/hexane which separated very well the starting material from the product. The work up consisted of an extraction with ethyl acetate, washing with brine, drying the ethyl acetate layer with magnesium sulfate then evaporated. The product (0.12 g) was obtained with almost 100% yield after flash chromatography.

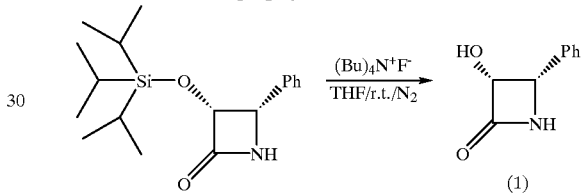

The next step in the synthesis is protection of the hydroxy group of the β-lactam with triethylsily chloride according to the following conditions:

The β-lactam (1) (0.12 g; 0.735 mmol) was dissolved in 10 ml pyridine at room temperature under nitrogen. The triethylsilyl chloride (0.40 ml; 2.38 mmol; 3.2 eq) was added at room temperature and the reaction was complete after one hour at room temperature. The work up consisted on quenching the reaction with saturated ammonium chloride, extract with methylene chloride, wash the methylene chloride solution with brine and dry the methylene chloride layer with magnesium sulfate. After filtration the solvent was evaporated. Most of the pyridine which was left behind was evaporated with heptane before running a flash chromatography with a 7.5" small column with 30% ethylacetate/hexane and collected the fractions 24–45 (0.129 g). The yield of the combined two steps is 74%. The NMR was in accord with structure 2.

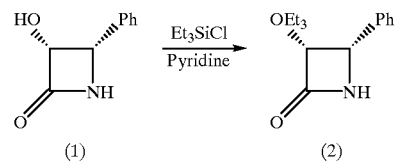

Next step is specific to the side chain we want to add. Here we will show the experimental for the side chain of canadensol and in the next page the coupling reaction with the protected baccatin derivative.

The triethyl-silyl-protected β-lactam (2) (0.030 g; 0.108 mmol) was dissolved in 1.5 ml dry methylene chloride under nitrogen at room temperature, triethylamine (41 μl; 0.294 mmol; 2.7 eq.) a trace of 4-DMAP (4-dimmethylaminopyridine), the solution was cooled in an ice water bath and isobutyryl chloride (0.025 ml; 0.239 mmol; 2.2 eq.) was stirred at room temperature for 3 hours when the reaction was complete. The work up consisted on quenching the reaction with saturated ammonium chloride, extract with methylene chloride, wash the methylene chloride solution with brine and dry the methylene chloride layer with magnesium sulfate. After filtration the solvent was evaporated and flash chromatography with 25% ethyl acetate/hexane in a 6" chromatography column 0.034 g of the required β-lactam (90% yield) (3) for the semi synthesis of canadensol was obtained.

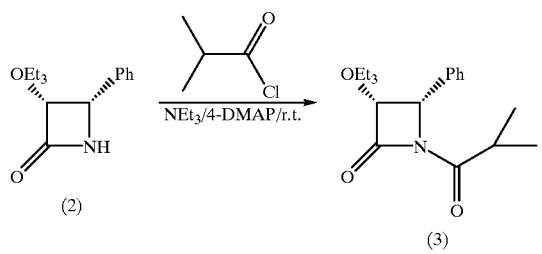

Coupling reaction: the C-7 triethylsilylprotected baccatin III (0.048 g; 0.0685 mmol) and the triethylsily-isopropyl-β-lactam (3) (0.043 g; 0.0978 mmol; 1.4 eq.) were dissolved in 3.6 ml dry tetrahydrofuran. The solution was cooled to a temperature in the range −45° C. to −50° C. (dry ice-acetonitrile bath) under nitrogen. The base sodium bistrimethylsilylamide (NaHMDS) (1.0 M) solution in tetrahydrofuran; 0.175 ml; 175 mmol; 2.6 eq) was added in one portion at a temperature of −45° C. and the reaction was stirred for 30 min at this temperature. The solution became yellow and was quenched at 30 min with an ammonium chloride saturated solution. The work up consisted of quenching the reaction with saturated ammonium chloride, extracting with ethyl acetate, washing the organic phase with brine and drying the organic layer with magnesium sulphate. After filtration the solvent was evaporated and flash chromatography of the residue with 20% ethyl acetate/hexane in a 6" chromatography column; 36 mg of the coupled protected taxane (5) was obtained with 14 mg of starting material recovered (4, uncoupled protected baccatin III).

Preparation of canadensol:

The deprotection of compound 5 was completed with 0.3 M HCl in 95% ethanol at 4° C. overnight. At this stage the reaction was complete, the reaction mixture cooled in an ice-water bath; ice added to reaction mixture and the pH adjusted to 5–6 with the dropwise addition of a saturated sodium bicarbonate solution. The reaction mixture is extracted four times with ethyl acetate, the organic phase washed with brine, the organic layer dried with MgSO$_4$, filtered and the solvent evaporated. The residue was subjected to flash chromatography with 75% ethyl acetate/hexane in a 7" mini column and 0.024 g of canadensol (6) was obtained with identical NMR and high resolution mass spectrometry as the canadensol obtained by Denis et al. method.

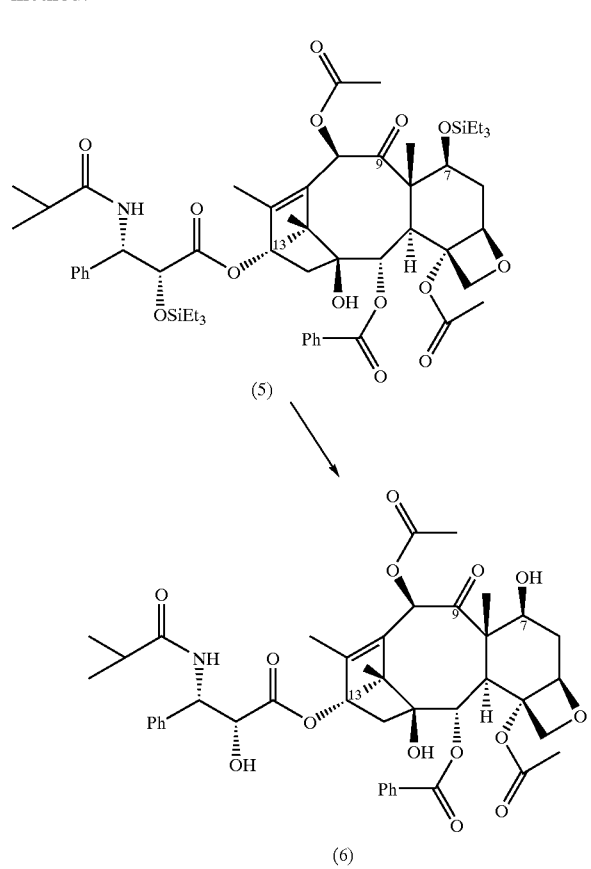

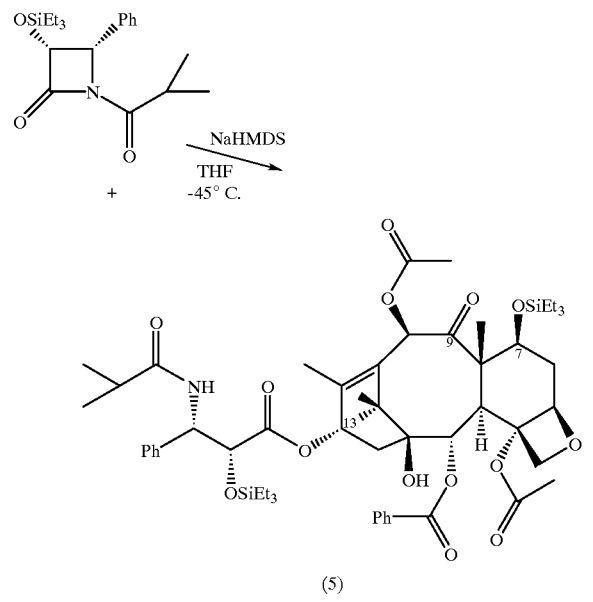

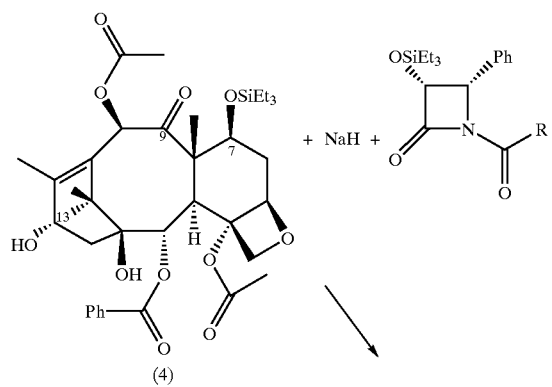

Scheme III

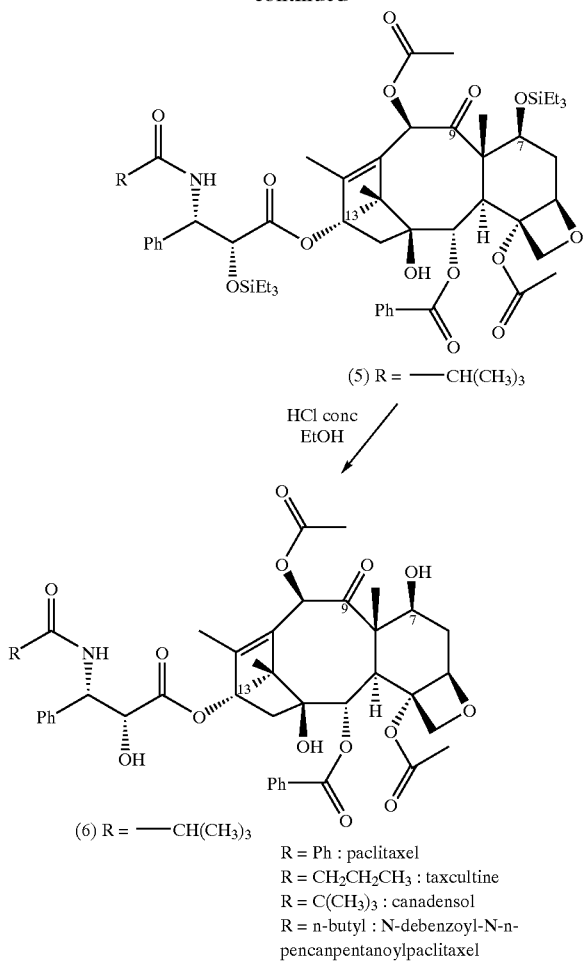

R = Ph : paclitaxel
R = CH₂CH₂CH₃ : taxcultine
R = C(CH₃)₃ : canadensol
R = n-butyl : N-debenzoyl-N-n-pencanpentanoylpaclitaxel

EXAMPLE 5

In Vitro Microtubule Assay

Tubulin is obtained by the purification of calf brain (Williams Jr, R. C. and J. C. Lee, Methods in Enzymology, 85:376, 1982). The taxanes to be tested are dissolved in dimethylsulfoxide (DMSO) with a final concentration of 10 $\mu$M. The methodologies used in this microtubule assay are well known to those skilled in the art. The method briefly consists of mixing the buffer and other required ingredients in a cuvette in an ice bath, with the DMSO solution containing the taxane to be analysed. Before the start of the measurement, the tubulin is added and the cuvette is set in a thermostatically controlled cell compartment of a UV-VIS spectrophotometer. The temperature is set at 37° C. to start the polymerisation of the tubulin. The control is performed with all the same ingredients just without the added taxane. Since bio-active taxanes cause tubulin to polymerize to microtubules and stabilize them, the turbidity of the mixture will rise and causing a corresponding increase in the absorbance observed at 350 nm. Theoretically, the faster the increase in absorbance, the more active the taxane.

As shown in FIGS. 1–4, Canadensol is more active than paclitaxel and taxcultine in these tests.

FIG. 1 illustrates that, at the same concentration, semi-synthetic Canadensol (ssC) causes higher degree of tubulin polymerisation than Paclitaxel (P).

Figure 2:
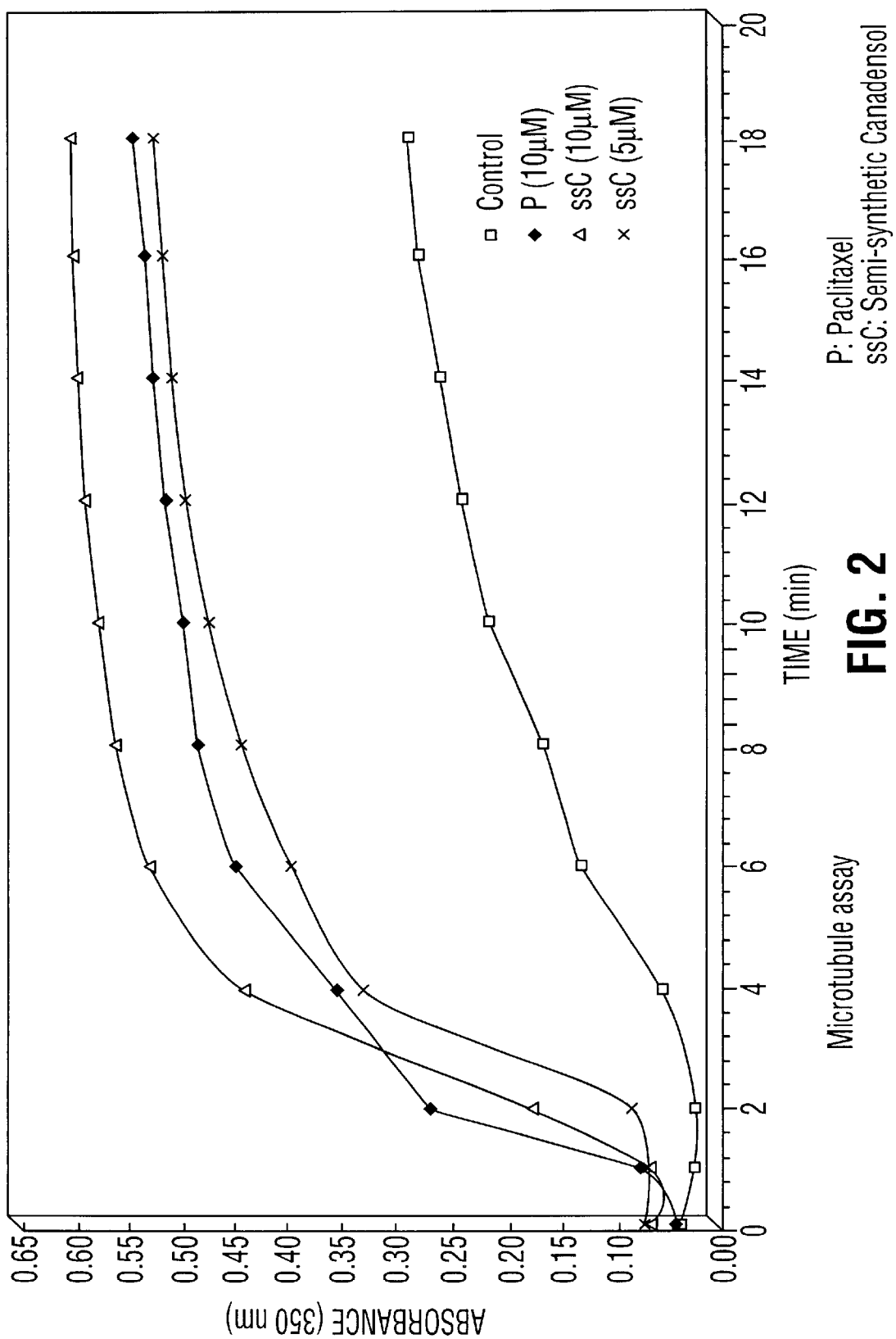
FIG. 2 shows the results of a microtubule assay demonstrating a concentration dependent antimitotic effect of Canadensol and that Canadensol is more active than paclitaxel at the same concentration.

FIG. 2 illustrates that 5 $\mu$M semi-synthetic Canadensol (ssC) appears to cause a similar degree of tubulin polymerisation as 10 $\mu$M Paclitaxel (P), this figure also emphasizes the dose-dependent response of tubulin polymerisation to semi-synthetic Canadensol (ssC) at concentrations of 5 $\mu$M and 10 $\mu$M.

Figure 3:
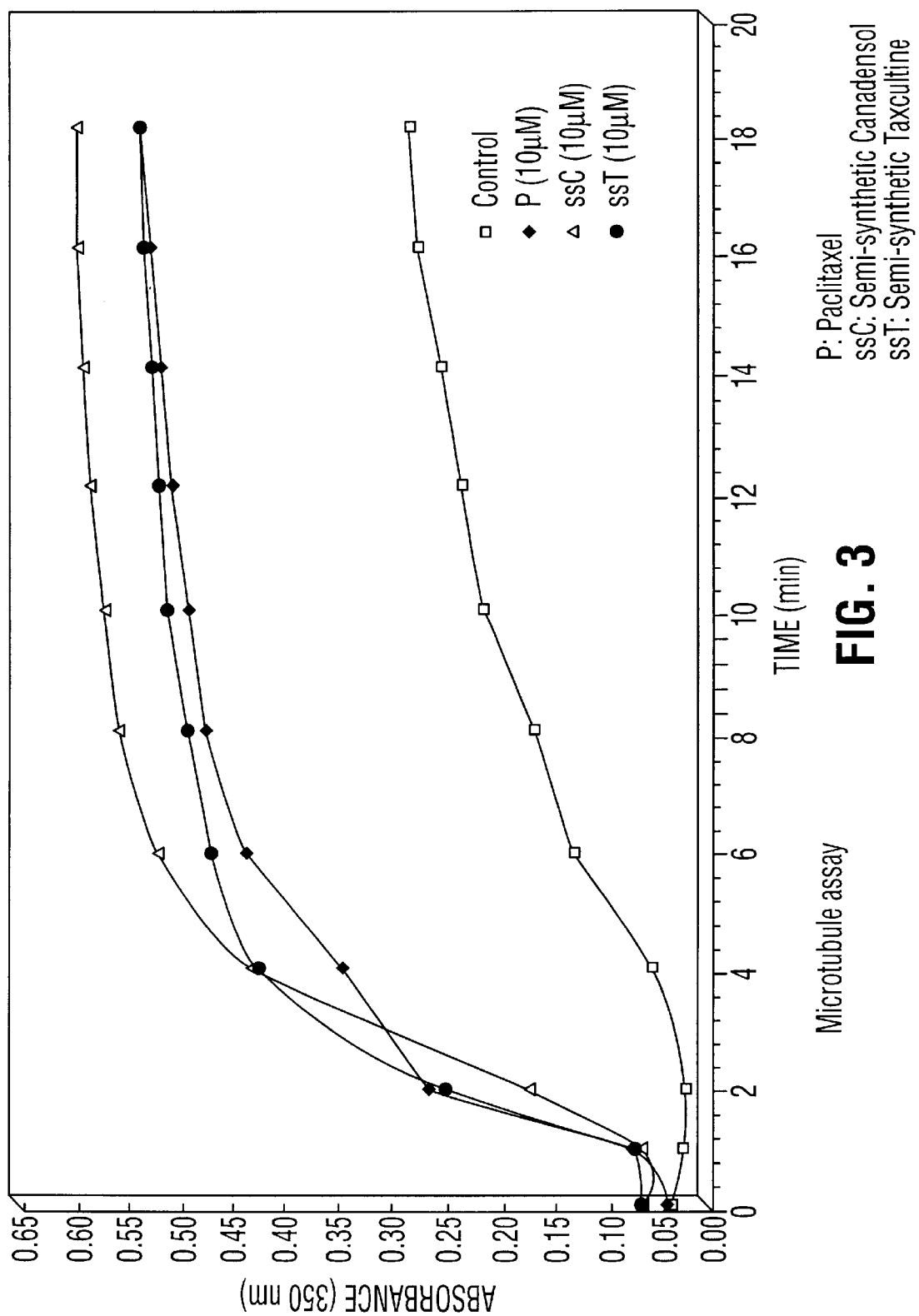
FIG. 3 demonstrates in a microtubule assay that, at the same concentration, paclitaxel and taxcultine exhibit similar antimitotic activity, but in the same experiment, Canadensol is more effective.

FIG. 3 illustrates that, at the same concentration (10 $\mu$M), semi-synthetic Canadensol (ssC) exhibits greater enhancement of tubulin polymerisation than semi-synthetic Taxcultine (ssT) or paclitaxel (P).

Figure 4:
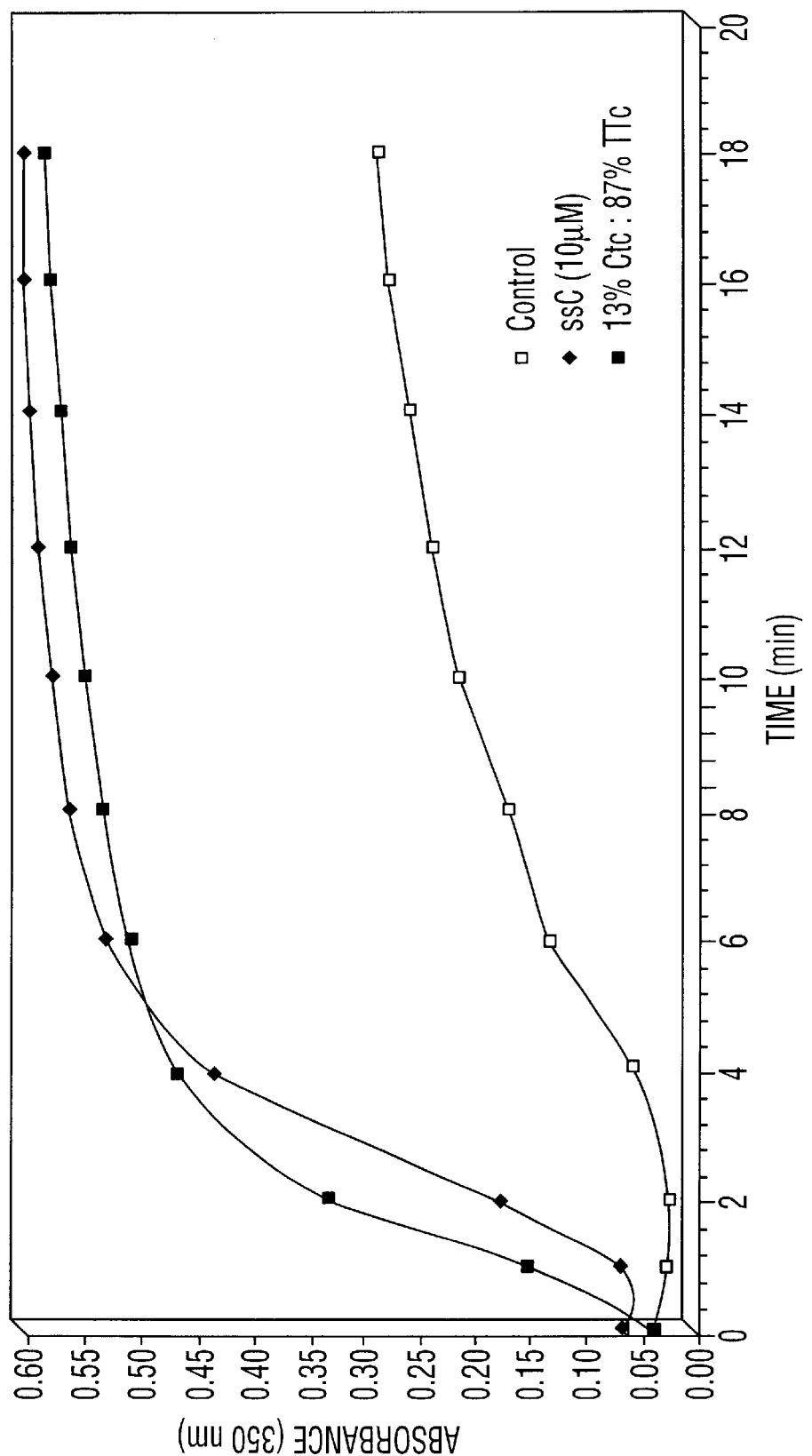
FIG. 4 shows the activity of semi-synthetic Canadensol versus that of a natural product prior to removing the taxcultine in a microtubule assay.

FIG. 4 illustrates that semi-synthetic Canadensol (ssC) obtained by the method described in the preferred embodiment of this invention shows similar activity to a mixture of 13% Canadensol and 87% Taxcultine purified from *Taxus canadensis*.

EXAMPLE 6

Preclinical Studies with Taxoids

Methods

1-Cell lines and cell culture.

The human ovarian adenocarcinoma cell line A2780 was used to evaluate the antiproliferative activity of taxoids. These cells were grown in either RPMI medium supplemented with 10% fetal bovine serum and penicillin-streptomycin antibiotics. Cells were maintained in culture at 37° C. in an atmosphere of 5% $CO_2$.

2-Cytotoxicity assay.

Exponentially growing cells (2–3×10³ cells/100 ml) were seeded in 96-well plates and incubated for 16 h. Cells were then treated continuously with the extracts. 72 h later, cell survival was evaluated by replacing the culture media with 150 ml fresh medium containing 10 mM 4-(2-hydroxyethyl)-1-piperazinecthamesulfonic acid buffer, pH 7.4, and 50 ml of 2.5 mg/ml of 3-(4,5-dimethylthiazo-2-yl)-2,5-diphenyltetrazolium bromide (MTT) in PBS, pH 7.4, were then added. After 3–4 h of incubation at 37° C., the medium and MTT were removed, and 200 ml of DMSO was added to dissolve the precipitate of reduced MTT, followed by addition of 25 ml glycine buffer (0.1M glycine plus 0.1M NaCl, pH 10.5). The formazan crystals were then dissolved and the absorbance was determined at 570 nm with a microplate reader (BIORAD, model 450). The MTT assay distinguished between viable and non-viable cells on the basis for the requirement of physiologically active mitochondria to metabolize the MTT only in viable cells. The $IC_{50}$ was calculated as the concentration of drug causing a 50% inhibition in the absorbance compared to cells treated with solvent alone, Table I.

In vivo study using GA3 cell model

Origin:

The DA3 cell line used in this study was derived from a hyperplastic mammary outgrowth (preneoplastic lesion) treated with 7,12-dimethylbenzanthracene (DMBA). DMBA-treated explant was then transplanted into the mammary glands of a female BALB/c mouse, and the resulting tumor was used to establish the DA3 cell line. DA3 is an immunogenic and non-metastatic mammary adenocarcinoma.

Source:

The cell line used in our study was originally obtained from Dr. Medina in 1993. Stocks of these cells were generated and stored during early passages in liquid nitrogen. One vial from this early stock was cultured and cells generated were used to confirm the absence of viral and mycoplasma infections. Cells were then propagated and stocks of these cells were established and stored in liquid nitrogen for further studies with Dup compounds.

Cell culture:

DA3 cells were maintained in RPMI 1640 medium supplemented with 1M mercaptoethanol, 1M Hepes buffer solution, 100 mM sodium pyruvate, 200 mM L-glutamine, 10 mM non-essential amino acids, 1M vitamins, 10% fetal bovine serum, 1% penicillin-streptomycin. Cells were maintained at 37° C. under 5% $CO_2$. Under these conditions, DA3 cells proliferate but do not differentiate.

Animal.

Female BALB/c mice (Charles River Inc.) were used to grow DA3 tumors. Mice were maintained at the Lady Davis Institute [LDI] Animal Care Facility. The animal facility is located in the basement of the LDI and is completely isolated from the research laboratories and administrative offices. Animal rooms are segregated from surgery rooms, offices, autoclaves, incinerators, and access to the animal facility is strictly limited to animal users only. Animal room used in our studies has two doors, one serving as the entrance, and the other door provides direct access to washing/sterilization/incineration facilities. It permits accurate adjustment of environmental parameters including temperature, humidity, ventilation, and lighting. Cleaning and sanitation practices are performed, on a daily basis, by personnel with appropriate training.

Tumor cell inoculation and treatments.

After one week acclimatisation, mice were randomized into a group of 5 per cage. Cages were randomly assigned to specific experimental groups. The mice were then labeled by numbers using the "ear punching" method. DA3 cells were transplanted subcutaneously to mice, as a suspension of tumor cells [$1 \times 10^6$ viable cells per 0.1 ml], in the right flank. All animals were inoculated at the same site.

For tumor induction, cells were grown to 70% confluence in complete medium and then collected using trypsin-EDTA solution [0.05% trypsin, 0.53 mM EDTA-4Na in HBSS $Ca^{++}$, $Mg^{++}$ and $NaHCO_3$ free], cells were then centrifuged and washed three times with phosphate buffer solution and resuspended at a dilution of 0.1 to $1 \times 10^6$ cells/0.1 ml. Viability was examined by trypan blue staining and only flasks in which the viability was $\geq 95\%$ were used for in vivo studies.

Treatment was initiated when tumors become palpable. Drug was given twice (day 1 and day 3) by iv. Control animals were given the same volume of saline solution. The dose of each drug was normalized to mouse body weight.

Tumor measurement.

Animals were examined every day but the tumor growth was monitored every second or third day using calipers. Parameters measured are: tumor measured along the longest axis (length) and the perpendicular shortest axis (width) and the relative tumor volume (in $cm^3$) was calculated by the formula: [Length (cm)×(width cm)$^2$]/2. Tumors which reach the limit size permitted by the Canadian regulation on the use of laboratory animals, or showing any apparent distress or discomfort were immediately sacrificed independently of the experimental protocol [usually 2–3 $cm^3$ but this depend on animal status and the decision is taken by the animal room personnel]. Animals were subjected, on a daily basis, to general examination.

Statistical analysis.

The unpaired Student t-test was used to compare statistical significance among various groups.

Results

In vitro studies

Figure 6:
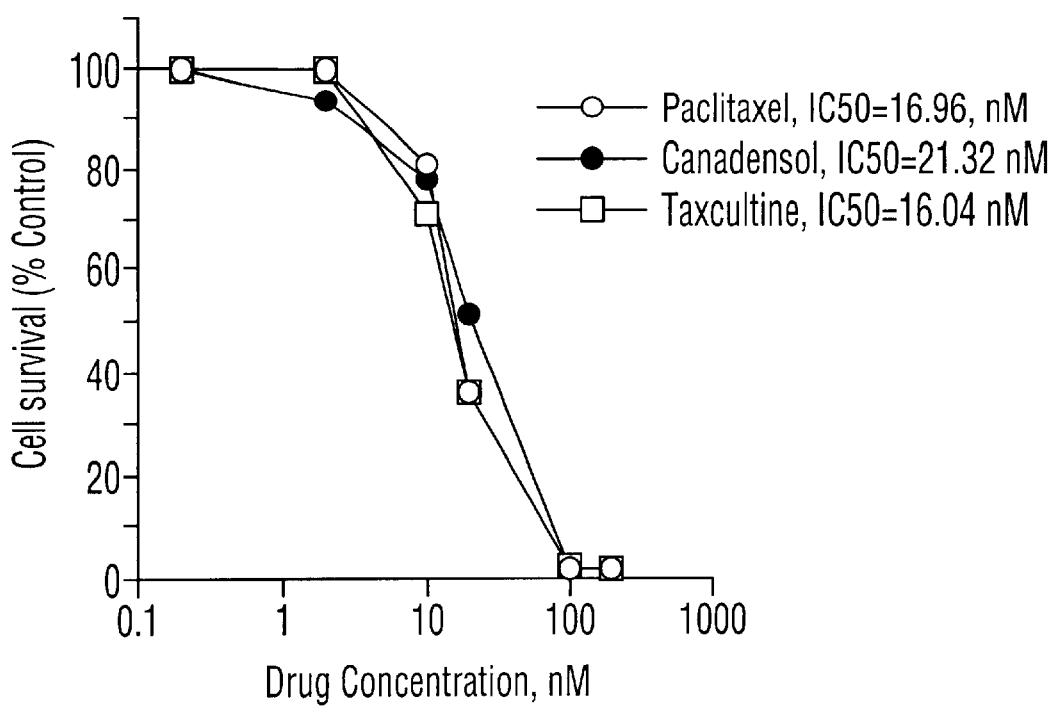
FIG. 6 shows the in vitro cycotoxic effects of taxoids (paclitaxel, Canadensol, and taxcultine) on A2780 cells versus taxoid concentration.
Figure 7:
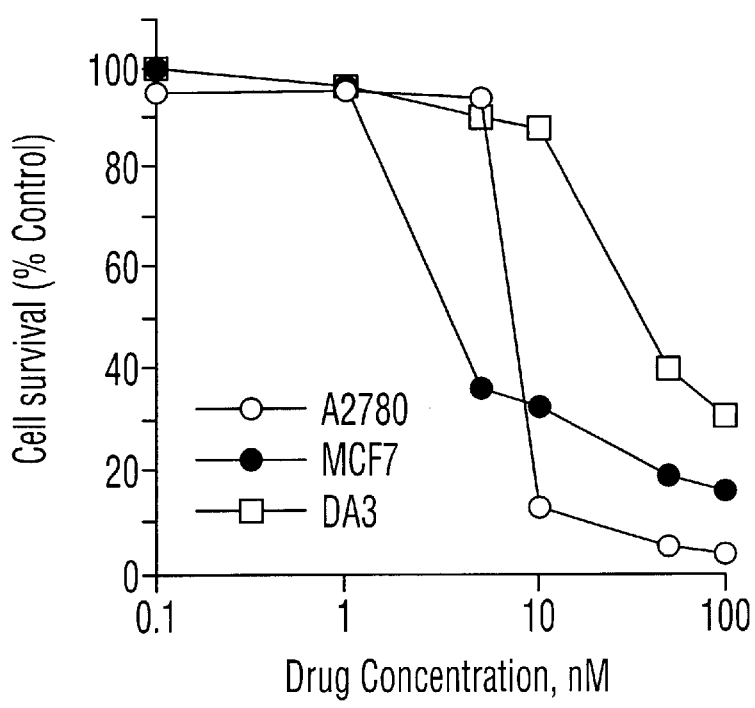
FIG. 7 shows the in vitro cytotoxic effects of paclitaxel on A2780, MCF7 and DA3 cells verses Paclitaxel concentration.

Canadensol was found to be as active as paclitaxel or taxcultine, in inhibiting the growth of the human ovarian carcinoma cell line, A2780, as shown in FIGS. 6, 7 and Table I.

In vivo studies

Figure 8A:
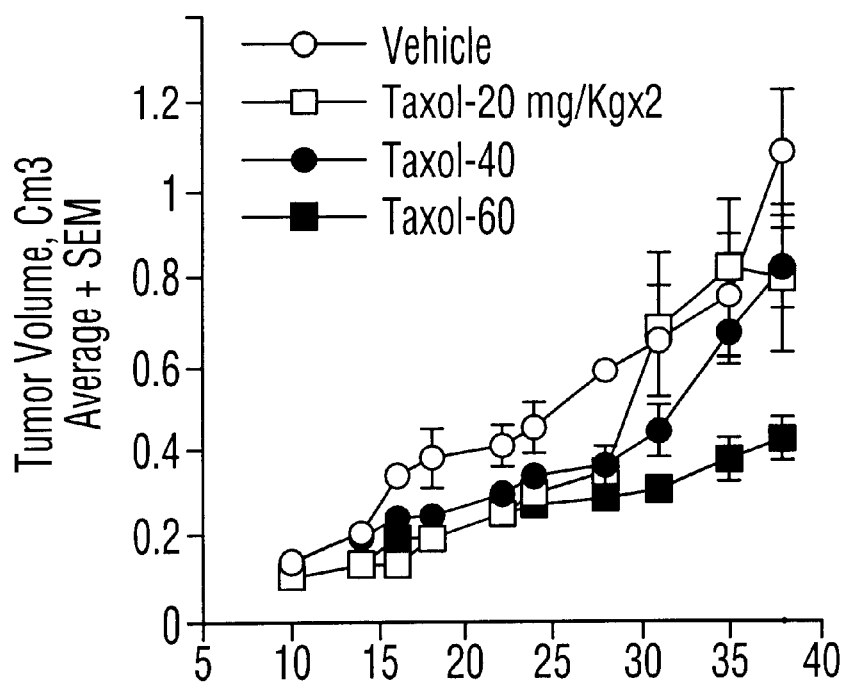
FIG. 8A shows the perturbation of tumour volume with differing doses of Taxol® versus time.
Figure 8B:
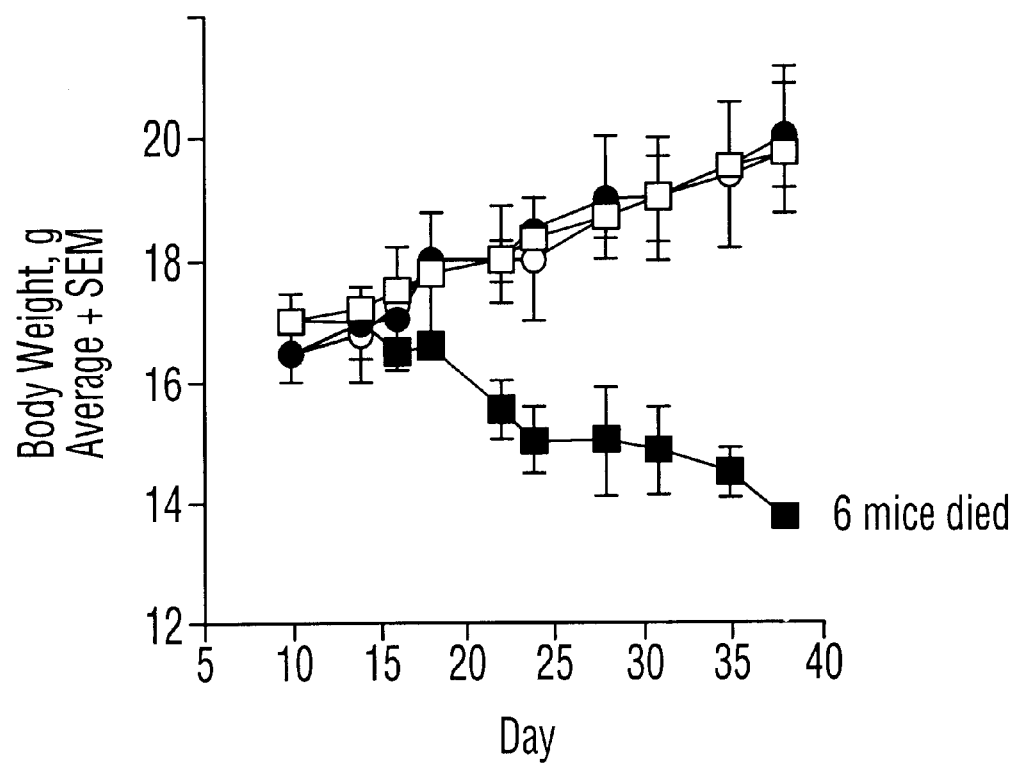
FIG. 8B shows the perturbation of body weight with differing doses of Taxol® versus time.
Figure 9:
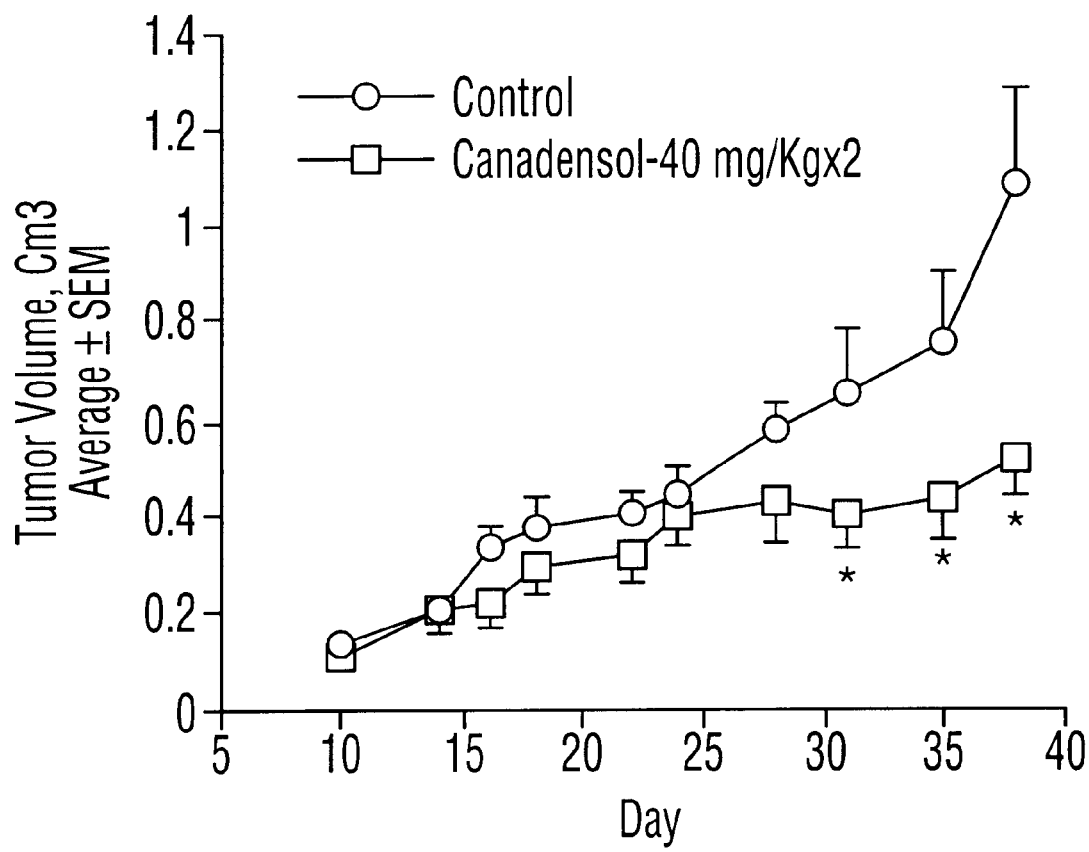
FIG. 9 shows the perturbation of tumour volume with differing doses of Canadensol and a control sample versus time.
Figure 10:
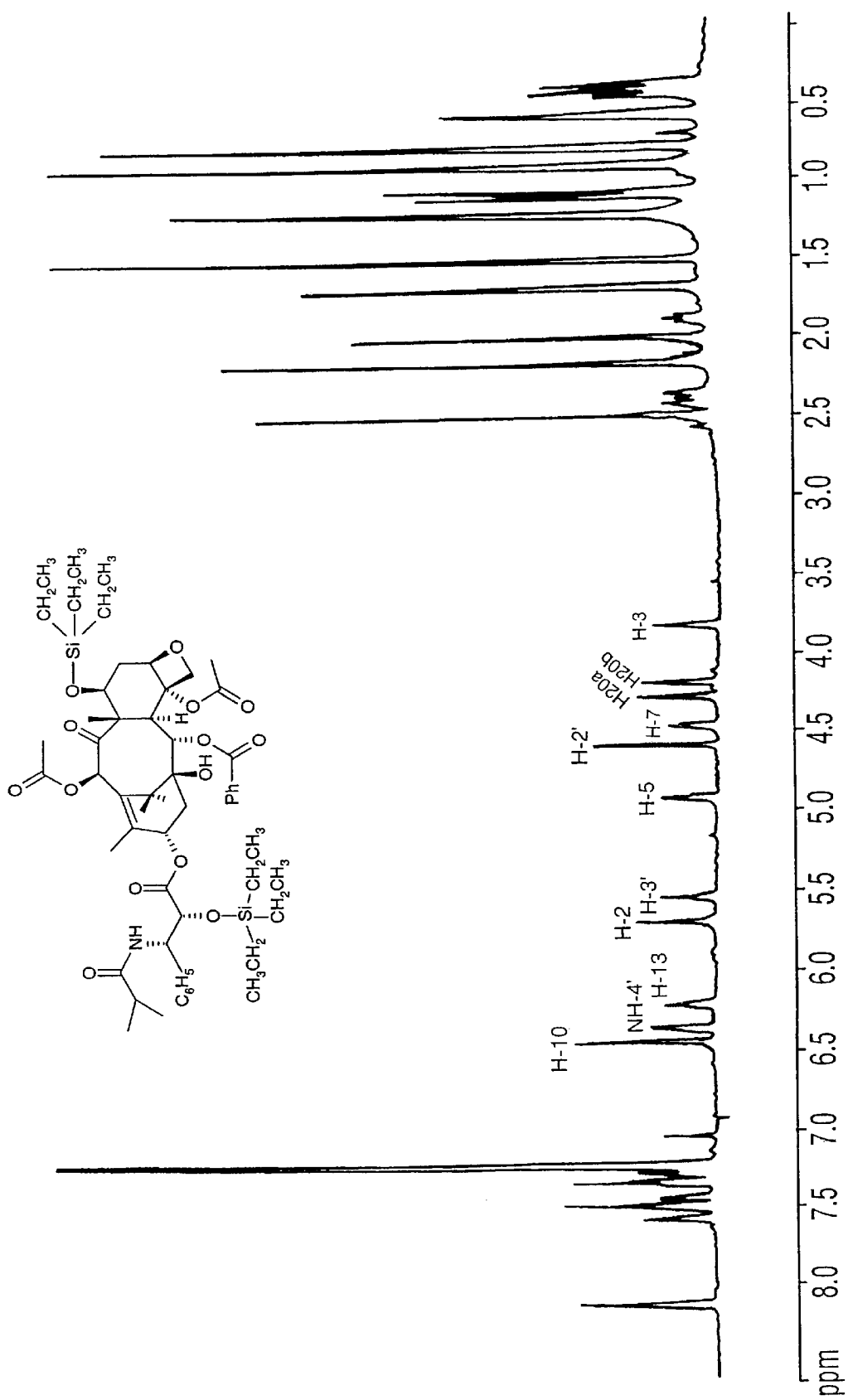

The mouse mammary adenocarcinoma tumors were resistant to paclitaxel since no significant antitumor activity was observed with tolerable doses (20–40 mg/Kg). Higher doses of paclitaxel were found to be very toxic (body weight loss and mortality), see FIG. 8B. Canadensol, however, was found to induce antitumor activity when given twice at 40 mg/kg, see FIG. 9. This effect was significant from day 30 to day 40 of tumor growth. No toxic effect was observed at this dose.

TABLE I

| A2780 Conc.(nM) | Abs | % | $I_{50}$ |
|---|---|---|---|
| TAXOL | | | |
| 0 | 1.433 | 100.00% | |
| 0.2 | 1.455 | 101.54% | |
| 2 | 1.464 | 102.16% | |
| 10 | 1.162 | 81.09% | 16.96 |
| 20 | 0.522 | 36.34% | |
| 100 | 0.021 | 1.47% | |
| 200 | 0.02 | 1.40% | |
| CANADENSOL | | | |
| 0 | 1.308 | | |
| 0.2 | 1.598 | 100.00% | |
| 2 | 1.504 | 94.12% | |
| 10 | 1.246 | 77.97% | |
| 20 | 0.812 | 50.81% | 21.32 |
| 100 | 0.026 | 1.63% | |
| 200 | 0.018 | 1.13% | |
| TAXCULTINE | | | |
| 0 | 1.155 | | |
| 0.2 | 1.535 | 100.00% | |
| 2 | 1.536 | 100.07% | |
| 10 | 1.093 | 71.21% | 16.04 |
| 20 | 0.554 | 36.09% | |
| 100 | 0.032 | 2.08% | |
| 200 | 0.022 | 1.43% | |

The embodiments of the invention in which an exclusive property or privilege is claimed are defined as follows:

1. A process for the preparation of a compound of formula III:

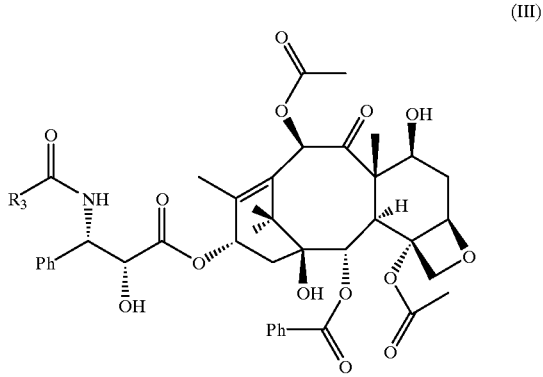

(III)

where $R_3$ is selected from the group consisting of n-propyl, isopropyl and n-butyl, or a pharmaceutically acceptable salt thereof; which comprises:

(a) deprotecting a compound of formula IV:

(IV)

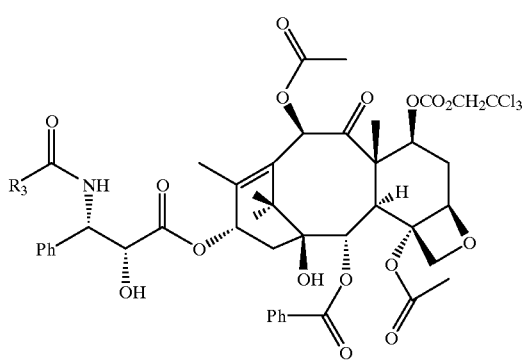

wherein $R_3$ is selected from the group consisting of n-propyl, isopropyl and n-butyl; or:

(b) treating the compound of formula V:

(V)

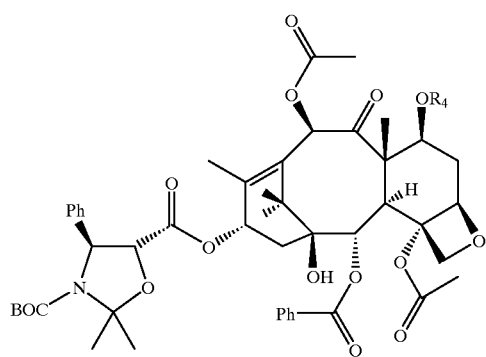

wherein $R_4$ is —$SiEt_3$; with organic acid, followed by an acylation step using bicarbonate and an acyl chloride in a one pot reaction, or (c) deprotecting a compound of formula VI:

(VI)

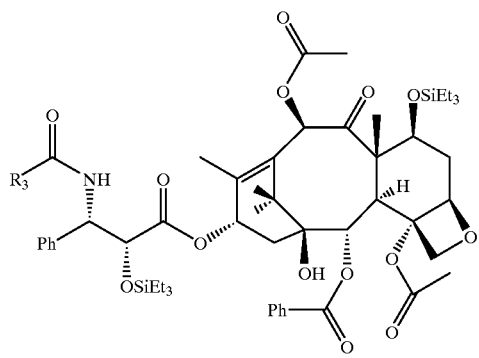

wherein $R_3$ is selected from the group consisting of n-propyl, isopropyl and n-butyl.

2. The process as in claim 1, wherein said acyl chloride is isobutyryl chloride, butyryl chloride or valeryl chloride.

3. The process as in claim 1, wherein said organic acid is formic acid.

4. The process as in claim 1, wherein $R_3$ is isopropyl.

5. The process as in claim 1, wherein $R_3$ is n-propyl.

6. The process as in claim 1, wherein $R_3$ is n-butyl.

7. A process for the preparation of the compound of formula IV:

(IV)

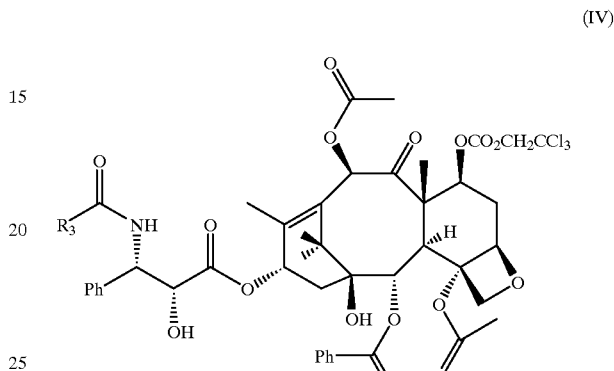

wherein $R_3$ is selected from the group consisting of n-propyl, isopropyl and n-butyl; which comprises treating the compound of formula V:

(V)

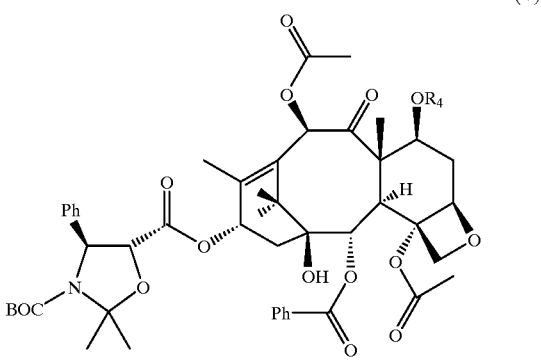

wherein $R_4$ is $CO_2CH_2CCl_3$, with an organic acid, followed by an acylation step using bicarbonate and an acyl chloride in a one pot reaction.

8. The process as in claim 7, wherein said acyl chloride is isobutyryl chloride, butyryl chloride or valeryl chloride.

9. The process as in claim 7, wherein said organic acid is formic acid.

10. The process as in claim 7, wherein $R_3$ is isopropyl.

11. The process as in claim 7, wherein $R_3$ is n-propyl.

12. The process as in claim 7, wherein $R_3$ is n-butyl.

13. A compound of formula VI:

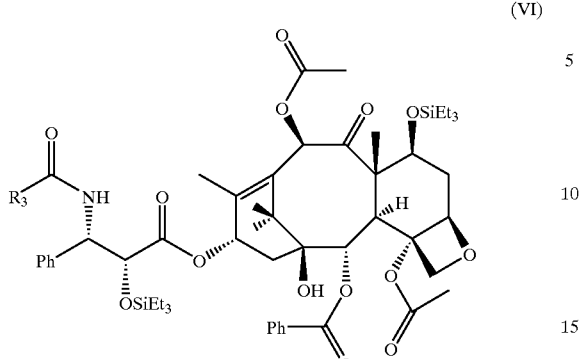

(VI)

wherein $R_3$ is selected from the group consisting of n-propyl, isopropyl and n-butyl.

14. The compound as in claim 13, wherein $R_3$ is isopropyl.

15. The compound as in claim 13, wherein $R_3$ is n-propyl.

16. The compound as in claim 13, wherein $R_3$ is n-butyl.

17. A process for the preparation of compound of claim 13, which comprises of the steps of (a) protecting the hydroxy group at the 7 position of baccatin III:

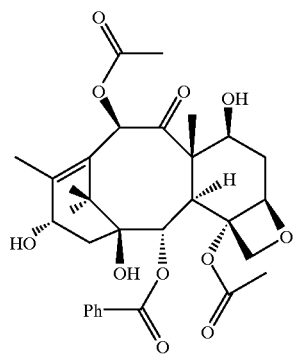

to form a 7-OH protected baccatin III; and (b) reacting the 7-OH protected baccatin III with a compound of formula VIII:

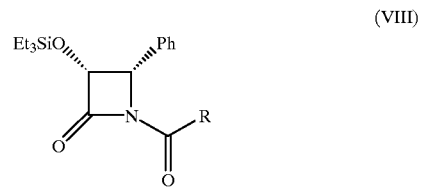

(VIII)

wherein $R_3$ is selected from the group consisting of n-propyl, isopropyl and n-butyl.

18. The process as in claim 17, wherein the hydroxy group is protected by reacting with $Et_3SiCl$ or $Cl_3CCH_2C(O)OCl$.

19. The process of claim 17, wherein $R_3$ is isopropyl.

20. The process of claim 17, wherein $R_3$ is n-propyl.

21. The process of claim 17, wherein $R_3$ is n-butyl.

* * * * *